US011141357B2

(12) United States Patent
Fik et al.

(10) Patent No.: US 11,141,357 B2
(45) Date of Patent: Oct. 12, 2021

(54) DENTAL ADHESIVE

(71) Applicants: Christoph P. Fik, Schonenberg (CH); Sven Pohle, Constance (DE); Huaibing Liu, Dover, DE (US); Joachim Klee, Radolfzell (DE)

(72) Inventors: Christoph P. Fik, Schonenberg (CH); Sven Pohle, Constance (DE); Huaibing Liu, Dover, DE (US); Joachim Klee, Radolfzell (DE)

(73) Assignee: DENTSPLY SIRONA Inc., York, PA (US)

(*) Notice: Subject to any disclaimer, the term of this patent is extended or adjusted under 35 U.S.C. 154(b) by 8 days.

(21) Appl. No.: 16/882,997

(22) Filed: May 26, 2020

(65) Prior Publication Data

US 2021/0137795 A1    May 13, 2021

Related U.S. Application Data

(63) Continuation of application No. 15/747,803, filed as application No. PCT/EP2016/067950 on Jul. 27, 2016, now abandoned.

(30) Foreign Application Priority Data

Jul. 27, 2015  (EP) .................... 15178515

(51) Int. Cl.
*A61K 6/887* (2020.01)
*C07D 295/185* (2006.01)
*C08L 33/10* (2006.01)
*C08L 33/26* (2006.01)
*A61K 6/71* (2020.01)
*A61K 6/77* (2020.01)
*A61K 6/813* (2020.01)
*A61K 6/818* (2020.01)
*C08F 220/54* (2006.01)
*C08F 220/56* (2006.01)

(52) U.S. Cl.
CPC ............... *A61K 6/887* (2020.01); *A61K 6/71* (2020.01); *A61K 6/77* (2020.01); *A61K 6/813* (2020.01); *A61K 6/818* (2020.01); *C07D 295/185* (2013.01); *C08F 220/54* (2013.01); *C08F 220/56* (2013.01); *C08L 33/10* (2013.01); *C08L 33/26* (2013.01)

(58) Field of Classification Search
CPC ...................................................... A61K 6/887
See application file for complete search history.

(56) References Cited

U.S. PATENT DOCUMENTS

2006/0069181 A1* 3/2006 Thalacker ............... A61K 6/889
                                                            523/116

FOREIGN PATENT DOCUMENTS

WO    WO-2014040729 A1 * 3/2014 ............... A61K 6/58

* cited by examiner

*Primary Examiner* — Michael F Pepitone
(74) *Attorney, Agent, or Firm* — Dentsply Sirona Inc.

(57) ABSTRACT

The present invention relates to an aqueous dental composition having a pH of at most 7. Furthermore, the present invention relates to the use of a specific composition for the preparation of an aqueous dental composition.

13 Claims, No Drawings

DENTAL ADHESIVE

This application is a continuation application of U.S. application Ser. No. 15/747,803, filed Jan. 26, 2018 (now abandoned).

FIELD OF THE INVENTION

The present invention relates to an aqueous dental composition having a pH of at most 7. Furthermore, the present invention relates to the use of a specific composition for the preparation of an aqueous dental composition. The aqueous dental composition according to the present invention may be a one-part dental composition. The aqueous dental composition according to the present invention has improved handling properties due to excellent wetting properties, among others due to improved penetration properties, and shows improved adhesive properties to both enamel and dentin. The aqueous dental composition according to the present invention also has high storage stability and excellent mechanical properties when cured.

BACKGROUND OF THE INVENTION

The restoration of dental structures is typically accomplished by the application of a dental adhesive and subsequently a restorative material to the dental structures. Dental adhesives are also used in the bonding of dental materials such as orthodontic appliances to a dental structure. In order to facilitate an intimate interaction between the dental composition and the dental structure, various pretreatment processes are often used in order to improve the bonding of the dental composition to dentin or enamel. A typical pretreatment may include etching and priming of the dental surface with the aim of fully wetting the dental structure with the dental composition.

However, given that etchants, primers, and adhesives are typically applied in a step-wise fashion, the restoration of dental structures is often a complex multistep procedure.

Accordingly, a need exists for simplifying conventional restorative or orthodontic procedures. For example, it would be desirable to provide a dental composition that accomplishes an intimate interaction between the dental structure and the dental composition without requiring separate etching and priming steps. A suitable dental composition could advantageously be formulated as an aqueous polymerizable dental compositions for use as a dental adhesive composition, a dental bonding agent, a pit and fissure sealant, a dental desensitizing composition, a pulp capping composition, a dental composite, dental glass ionomer cement, a dental cement or a dental root canal sealer composition. Moreover, a generic dental composition may be a dental infiltrant.

WO 2014/040729 A1 and its family member EP 2 705 827 A1 disclose an aqueous dental composition comprising a polymerizable allyl (meth)acrylamide compound preferably having two allyl(meth)acrylamide moieties, which may be linked via a straight chain or branched chain alkylene group or a cycloalkylene group. The allyl (meth)acrylamide compound has a favorable polymerization enthalpy and high hydrolysis stability. Dental compositions such as those disclosed in WO 2014/040729 A1 and EP 2 705 827 A1 have a viscosity which tends to be high.

EP 1 911 434 A1 discloses a dental composition containing a polymerizable acidic phosphoric acid ester monomer.

SUMMARY OF THE INVENTION

It is the problem of the present invention to provide an aqueous dental composition having a pH of at most 7, which has good wetting properties to a dental surface and an advantageous viscosity, whereby said dental composition may be polymerized to provide high adhesion to dentine and enamel, while the aqueous dental composition has high storage stability of the uncured dental composition and high stability after curing in the mouth of a patient.

The present invention provides an aqueous dental composition having a pH of at most 7, comprising:

(a) 1 to 70 percent by weight based on the total weight of the composition of a polymerizable compound of the following formula (I):

wherein
A is a group of the following formula (II)

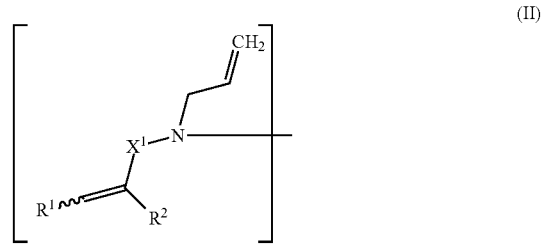

$X^1$ is CO, CS, $CH_2$, or a group $[X'Z]_k$, wherein X' is an oxygen atom, a sulfur atom or NH, Z is a straight chain or branched $C_{1-4}$ alkylene group, and k is an integer of from 1 to 10;

$R^1$ is a hydrogen atom,
—COOM,
a straight chain or branched $C_{1-16}$ alkyl group which may be substituted by a $C_{3-6}$ cycloalkyl group, a $C_{6-14}$ aryl or $C_{3-14}$ heteroaryl group, —COOM, —$PO_3M$, —O—$PO_3M_2$ or —$SO_3M$,
a $C_{3-6}$ cycloalkyl group which may be substituted by a $C_{1-16}$ alkyl group, a $C_{6-14}$ aryl or $C_{3-14}$ heteroaryl group, —COOM, —$PO_3M$, —O—$PO_3M_2$ or —$SO_3M$,
a $C_{6-14}$ aryl or $C_{3-14}$ heteroaryl group which may be substituted by —COOM, —$PO_3M$, —O—$PO_3M_2$ or —$SO_3M$, $R^2$ is a hydrogen atom,
—COOM
a straight chain or branched $C_{1-16}$ alkyl group which may be substituted by a $C_{6-14}$ aryl or $C_{3-14}$ heteroaryl group, —COOM, —$PO_3M$, —O—$PO_3M_2$ and —$SO_3M$,
a $C_{3-6}$ cycloalkyl group which may be substituted by a $C_{1-16}$ alkyl group, a $C_{6-14}$ aryl or $C_{3-14}$ heteroaryl group, —COOM, —$PO_3M$, —O—$PO_3M_2$ or —$SO_3M$, or
a $C_{6-14}$ aryl or $C_{3-14}$ heteroaryl group which may be substituted by —COOM, —$PO_3M$, —O—$PO_3M_2$ and —$SO_3M$, L is a divalent $C_{2-12}$ alkenylene linker group, which may contain 1 to 3 carbonyl groups or heteroatoms selected from oxygen, nitrogen and sulfur, and which may be substituted by a hydroxyl group, a $C_{6-14}$ aryl group, —COOM, —$PO_3M$, —O—$PO_3M_2$ or —$SO_3M$, wherein M is a hydrogen atom or a metal atom;

B is selected from
(i) a group according to the definition of A,
(ii) a group of the following formula (III)

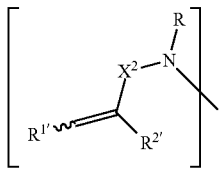   (III)

$X^2$ independently has the same meaning as defined for $X^1$ in formula (II), $R^{1'}$ and $R^{2'}$ are independent from each other and independently have the same meaning as defined for $R^1$ and $R^2$ in formula (II), R is a hydrogen atom,
  a straight chain or branched $C_{1-16}$ alkyl group which may be substituted by a $C_{3-6}$ cycloalkyl group, a $C_{6-14}$ aryl or $C_{3-14}$ heteroaryl group, —COOM, —PO$_3$M, —O—PO$_3$M$_2$ or —SO$_3$M,
  a $C_{3-6}$ cycloalkyl group which may be substituted by a $C_{1-6}$ alkyl group, a $C_{6-14}$ aryl or $C_{3-14}$ heteroaryl group, —COOM, —PO$_3$M, —O—PO$_3$M$_2$ or —SO$_3$M,
  a $C_{6-14}$ aryl or $C_{3-14}$ heteroaryl group which may be substituted by —COOM, —PO$_3$M, —O—PO$_3$M$_2$ or —SO$_3$M, (iii) a group of the following formula (IV)

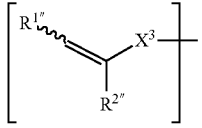   (IV)

wherein
$X^3$ is CO, —CH$_2$CO—, CS, or —CH$_2$CS—,
$R^{1''}$ and $R^{2''}$ which are independent from each other and independently have the same meaning as defined for $R^1$ and $R^2$ in formula (II), or (iv) a group $[Z'X'']_mE$,
  wherein
  Z' is a straight chain or branched $C_{1-4}$ alkylene group,
  X'' is an oxygen atom, a sulfur atom or NH,
  E is a hydrogen atom,
    PO$_3$M$_2$,
    a straight chain or branched $C_{1-16}$ alkyl group which may be substituted by a $C_{3-6}$ cycloalkyl group, a $C_{6-14}$ aryl or $C_{3-14}$ heteroaryl group, —COOM, —PO$_3$M, —O—PO$_3$M$_2$ or —SO$_3$M,
    a $C_{3-6}$ cycloalkyl group which may be substituted by a $C_{1-16}$ alkyl group, a $C_{6-14}$ aryl or $C_{3-14}$ heteroaryl group, —COOM, —PO$_3$M, —O—PO$_3$M$_2$ or —SO$_3$M,
    a $C_{6-14}$ aryl or $C_{3-14}$ heteroaryl group which may be substituted by —COOM, —PO$_3$M, —O—PO$_3$M$_2$ or —SO$_3$M, and
  m is an integer of from 1 to 10; and wherein M of any one $R^1$, $R^2$, L, R and E, which M are independent from each other, each represent a hydrogen atom or a metal atom;

(b) 2 to 20 percent by weight based on the total weight of the composition of a polymerizable compound of the following formula (V):

A'-L'-A'   (V)

wherein the
A' which are independent from each other, each represent a group of the following formula (VI)

   (VI)

wherein
$X^{2*}$ independently has the same meaning as defined for $X^1$ in formula (II), $R^{1*}$ and $R^{2*}$ are independent from each other and independently have the same meaning as defined for $R^1$ and $R^2$ in formula (II), R* is a hydrogen atom,
  a straight chain or branched $C_{1-16}$ alkyl group which may be substituted by a $C_{3-6}$ cycloalkyl group, a $C_{6-14}$ aryl or $C_{3-14}$ heteroaryl group, —COOM, —PO$_3$M, —O—PO$_3$M$_2$ or —SO$_3$M,
  a $C_{3-6}$ cycloalkyl group which may be substituted by a $C_{1-16}$ alkyl group, a $C_{6-14}$ aryl or $C_{3-14}$ heteroaryl group, —COOM, —PO$_3$M, —O—PO$_3$M$_2$ or —SO$_3$M,
  a $C_{6-14}$ aryl or $C_{3-14}$ heteroaryl group which may be substituted by —COOM, —PO$_3$M, —O—PO$_3$M$_2$ or —SO$_3$M, L' is a divalent $C_{2-12}$ alkylene linker group, which may contain 1 to 3 carbonyl groups or heteroatoms selected from oxygen, nitrogen and sulfur, and which may be substituted by a hydroxyl group, a $C_{6-14}$ aryl group, —COOM, —PO$_3$M, —O—PO$_3$M$_2$ or —SO$_3$M, wherein M is a hydrogen atom or a metal atom;

wherein M of any one $R^{1*}$, $R^{2*}$, L' and R*, which M are independent from each other, each represent a hydrogen atom or a metal atom;

(c) 1 to 20 percent by weight based on the total weight of the composition of one or more polymerizable monomers having one or more acidic groups;

(d) 0.001 to 5 percent by weight based on the total weight of the composition of an initiator system;

(e) 0.001 to 1 percent by weight based on the total weight of the composition of a stabilizer; and (f) 25 to 50 percent by weight based on the total weight of the composition of a solvent mixture comprising water and an organic solvent.

Furthermore, the present invention provides a use of a composition comprising (a) a polymerizable compound of the following formula (I):

A-L-B   (I)

wherein

A is a group of the following formula (II)

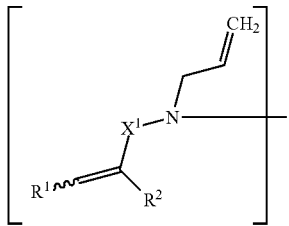
(II)

$X^1$ is CO, CS, $CH_2$, or a group $[X'Z]_k$, wherein $X'$ is an oxygen atom, a sulfur atom or NH, Z is a straight chain or branched $C_{1-4}$ alkylene group, and k is an integer of from 1 to 10;

$R^1$ is a hydrogen atom,
—COOM,
a straight chain or branched $C_{1-16}$ alkyl group which may be substituted by a $C_{3-6}$ cycloalkyl group, a $C_{6-14}$ aryl or $C_{3-14}$ heteroaryl group, —COOM, —$PO_3M$, —O—$PO_3M_2$ or —$SO_3M$,
a $C_{3-6}$ cycloalkyl group which may be substituted by a $C_{1-16}$ alkyl group, a $C_{6-14}$ aryl or $C_{3-14}$ heteroaryl group, —COOM, —$PO_3M$, —O—$PO_3M_2$ or —$SO_3M$,
a $C_{6-14}$ aryl or $C_{3-14}$ heteroaryl group which may be substituted by —COOM, —$PO_3M$, —O—$PO_3M_2$ or —$SO_3M$, $R^2$ is a hydrogen atom,
—COOM
a straight chain or branched $C_{1-16}$ alkyl group which may be substituted by a $C_{6-14}$ aryl or $C_{3-14}$ heteroaryl group, —COOM, —$PO_3M$, —O—$PO_3M_2$ and —$SO_3M$,
a $C_{3-6}$ cycloalkyl group which may be substituted by a $C_{1-6}$ alkyl group, a $C_{6-14}$ aryl or $C_{3-14}$ heteroaryl group, —COOM, —$PO_3M$, —O—$PO_3M_2$ or —$SO_3M$, or
a $C_{6-14}$ aryl or $C_{3-14}$ heteroaryl group which may be substituted by —COOM, —$PO_3M$, —O—$PO_3M_2$ and —$SO_3M$, L is a divalent $C_{2-12}$ alkenylene linker group, which may contain 1 to 3 carbonyl groups or heteroatoms selected from oxygen, nitrogen and sulfur, and which may be substituted by a hydroxyl group, a $C_{6-14}$ aryl group, —COOM, —$PO_3M$, —O—$PO_3M_2$ or —$SO_3M$, wherein M is a hydrogen atom or a metal atom;

B is selected from
(i) a group according to the definition of A,
(ii) a group of the following formula (III)

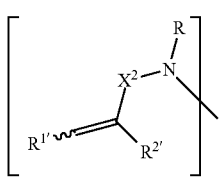
(III)

$X^2$ independently has the same meaning as defined for $X^1$ in formula (II), $R^{1'}$ and $R^{2'}$ are independent from each other and independently have the same meaning as defined for $R^1$ and $R^2$ in formula (II), R is a hydrogen atom,
a straight chain or branched $C_{1-16}$ alkyl group which may be substituted by a $C_{3-6}$ cycloalkyl group, a $C_{6-14}$ aryl or $C_{3-14}$ heteroaryl group, —COOM, —$PO_3M$, —O—$PO_3M_2$ or —$SO_3M$,
a $C_{3-6}$ cycloalkyl group which may be substituted by a $C_{1-16}$ alkyl group, a $C_{6-14}$ aryl or $C_{3-14}$ heteroaryl group, —COOM, —$PO_3M$, —O—$PO_3M_2$ or —$SO_3M$,
a $C_{6-14}$ aryl or $C_{3-14}$ heteroaryl group which may be substituted by —COOM, —$PO_3M$, —O—$PO_3M_2$ or —$SO_3M$, (iii) a group of the following formula (IV)

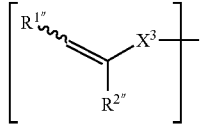
(IV)

wherein $X^3$ is CO, —$CH_2CO$—, CS, or —$CH_2CS$—, $R^{1''}$ and $R^{2''}$ which are independent from each other and independently have the same meaning as defined for $R^1$ and $R^2$ in formula (II), (iv) a group $[Z'X'']_mE$, wherein $Z'$ is a straight chain or branched $C_{1-4}$ alkylene group, $X''$ is an oxygen atom, a sulfur atom or NH, E is a hydrogen atom,
$PO_3M_2$,
a straight chain or branched $C_{1-16}$ alkyl group which may be substituted by a $C_{3-6}$ cycloalkyl group, a $C_{6-14}$ aryl or $C_{3-14}$ heteroaryl group, —COOM, —$PO_3M$, —O—$PO_3M_2$ or —$SO_3M$,
a $C_{3-6}$ cycloalkyl group which may be substituted by a $C_{1-16}$ alkyl group, a $C_{6-14}$ aryl or $C_{3-14}$ heteroaryl group, —COOM, —$PO_3M$, —O—$PO_3M_2$ or —$SO_3M$,
a $C_{6-14}$ aryl or $C_{3-14}$ heteroaryl group which may be substituted by —COOM, —$PO_3M$, —O—$PO_3M_2$ or —$SO_3M$, and m is an integer of from 1 to 10; and wherein M of any one $R^1$, $R^2$, L, R and E, which M are independent from each other, each represent a hydrogen atom or a metal atom; and (b) 2 to 20 percent by weight based on the total weight of the composition of a polymerizable compound of the following formula (V):

$$A'\text{-}L'\text{-}A' \qquad (V)$$

wherein the

A' which are independent from each other, each represent a group of the following formula (VI)

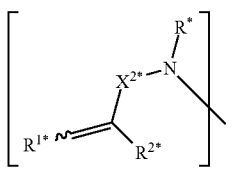

(VI)

wherein $X^{2*}$ independently has the same meaning as defined for $X^1$ in formula (II), $R^{1*}$ and $R^{2*}$ are independent from each other and independently have the same meaning as defined for $R^1$ and $R^2$ in formula (II), R* is a hydrogen atom, a straight chain or branched $C_{1-16}$ alkyl group which may be substituted by a $C_{3-6}$ cycloalkyl group, a $C_{6-14}$ aryl or $C_{3-14}$ heteroaryl group, —COOM, —PO$_3$M, —O—PO$_3$M$_2$ or —SO$_3$M, a $C_{3-6}$ cycloalkyl group which may be substituted by a $C_{11}$ alkyl group, a $C_{6-14}$ aryl or $C_{3-14}$ heteroaryl group, —COOM, —PO$_3$M, —O—PO$_3$M$_2$ or —SO$_3$M, a $C_{6-14}$ aryl or $C_{3-14}$ heteroaryl group which may be substituted by —COOM, —PO$_3$M, —O—PO$_3$M$_2$ or —SO$_3$M, L' is a divalent $C_{2-12}$ alkylene linker group, which may contain 1 to 3 carbonyl groups or heteroatoms selected from oxygen, nitrogen and sulfur, and which may be substituted by a hydroxyl group, a $C_{6-14}$ aryl group, —COOM, —PO$_3$M, —O—PO$_3$M$_2$ or —SO$_3$M, wherein M is a hydrogen atom or a metal atom;

wherein M of any one $R^{1*}$, $R^{2*}$, L' and R*, which M are independent from each other, each represent a hydrogen atom or a metal atom;

for the preparation of an aqueous dental composition.

The present invention is based on the recognition that a combination of a compound of formula (I) and a compound of formula (V) as defined above provides surprisingly improved wetting properties, among others due to improved penetration properties. It has been found that wetting of a dental surface by the aqueous dental composition and viscosity of the aqueous dental composition can be synergistically improved by a combination of polymerizable compounds of formulae (I) and (V) in an aqueous solvent mixture. Accordingly, the application of the aqueous dental composition on a dental surface is simplified and the wetting of the dental surface is improved.

Moreover, the specific combination of polymerizable compounds of formulae (I) and (V) is the basis for high storage stability of the aqueous dental composition and stability after curing in the mouth of a patient.

DETAILED DESCRIPTION OF PREFERRED EMBODIMENTS

The term "aqueous dental composition" relates to a composition comprising a solvent mixture comprising an organic solvent and water. Preferably, the solvent mixture comprises water in an amount of at least 1 percent by weight based on the total weight of the composition. Commercially available organic solvents may contain a substantial amount of water and therefore may serve as a source for the water contained in the solvent mixture. However, additional water, that is water which does not derive from the organic solvent of the solvent mixture, is preferably added to the organic solvent.

The "pH of at most 7" of the aqueous dental composition according to the invention may be adjusted by any means known in the art, e.g. by adding predetermined amounts of one or more acidic or alkaline compounds to the aqueous dental composition. In this context, the term "acidic compounds" denotes compounds having a $pK_a$ value within the range of about −10 to 50. The term "alkaline compounds" denotes compounds having a $pK_b$ value within the range of about −34 to 14. Examples of suitable inorganic acids are sulfuric acid, phosphonic acid, phosphoric acid, hydrochloric acid, nitric acid and the like, which may be used alone or in combination with each other. Examples of suitable organic acidic compounds are carboxylic acids which are preferably selected from the group consisting of formic acid, acetic acid, lactic acid, citric acid, itaconic acid, poly(meth)acrylic acid, itaconic acid, maleic acid, polyvinyl phosphonic acid, polyvinyl phosphoric acid, trifluoromethanesulfonic acid, toluenesulfonic acid, methanesulfonic acid, succinic acid, malic acid, tannic acid, toluene sulfonic acid, adipic acid, tartaric acid and ascorbic acid.

Examples of suitable inorganic alkaline compounds are alkali metal or earth alkaline metal hydroxides, for example sodium hydroxid, potassium hydroxide, calcium hydroxide or barium hydroxide, which may be used alone or in combination with each other. Examples of suitable organic alkalines are e.g. organic primary and tertiary amines such as triethanolamine and tris(hydroxymethyl)-aminomethan (TRIS). The set pH-value of the aqueous dental composition may be stabilized by means of a typical chemical buffer system, that is a combination of a weak organic or inorganic acid having a $pK_a$ value at a temperature of 20° C. within the range of about 9 to 50 and its corresponding salt.

Alternatively, the buffer system may be in the form of a Norman Goods buffer (Good's buffer) representing organic compounds having a $pK_a$ value at a temperature of 20° C. in a range between about 6 and 8, having biochemical inertness and being suitable for application in a biological system such as the human body. Examples for typical chemical buffer systems are acidic acid/acetate buffer, dihydrogenphosphate/monohydrogenphosphate buffer or a citric acid/citrate buffer.

Examples for Good's buffers are 4-(2-hydroxyethyl)-1-piperazineethanesulfonic acid (HEPES), 2-(N-morpholino) ethanesulfonic acid (MES) or N-cyclohexyl-3-aminopropanesulfonic acid (CAPS). In connection with the term "pH-value" it is noted that the pH-value/system typically relates to aqueous systems wherein water is the main compound, i.e. present in an amount of about 90 percent by weight. In the present aqueous dental composition, water is typically not the main component. However, all pH-values indicated in the present application relate to pH-values determined by suitable standard means for determining the pH-value of aqueous systems, e.g. by means of a glass electrode.

Besides of the aforementioned organic acidic and alkaline compounds, the compounds according to any one of items (a), (b), (c), (d), (e) and (f) may be applied for setting the pH of the present aqueous dental composition. For example, the polymerizable compound of formulae (I) and (V) according to (a) and (b) may have an acidic functional group such as —COOM, —PO$_3$M, —O—PO$_3$M$_2$ or —SO$_3$M, wherein M may represent a hydrogen atom and thus influences the pH of the present aqueous dental composition. Besides, the polymerizable monomer according to (c) mandatory has one or more acidic groups. On the other hand, the polymerizable compounds of formulae (I) and (V) according to (a) and (b) mandatory comprise an alkaline functional group in the form of a tertiary amine group.

The term "polymerizable" as used herein in connection with "polymerizable compounds" of formulae (I) and (V), "polymerizable monomer having one or more acidic group", "polymerizable group" and "polymerizable double bond" respectively mean any compound, monomer, functional group or double bond capable of radical polymerization. Preferably, capability of radical polymerization is provided by a carbon-carbon double bond. Examples of the polymerizable carbon-carbon double bonds include vinyl, conjugated vinyl, allyl, acryl, methacryl and styryl. More preferably, the polymerizable carbon-carbon double bound is selected from the group consisting of acryl, methacryl, allyl and styryl.

The term "alkenylene" as used herein in connection with group L of compound of formula (I) means a divalent group derived from a straight- or branched-chain $C_{2-12}$ hydrocarbon which contains at least one carbon-carbon double bond.

The term "alkylene" as used herein in connection with group L' of compound of formula (V) means a divalent group derived from a straight- or branched-chain saturated $C_{2-12}$ hydrocarbon.

In both of the above defined "alkenylene" and "alkylene" defined for L and L', apart from the 2 to 12 carbon atoms of the hydrocarbon, in addition, the hydrocarbon may contain further carbon atoms deriving from optional carbonyl groups incorporated therein, optional substitution with $C_{6-14}$ aryl group and/or an optional —COOM group.

The compounds of formulae (I) and (V) are hydrolysis-stable. This means that these compounds are stable to hydrolysis in an acidic medium, such as in a dental composition. Specifically, these compounds do not contain groups such as ester groups which hydrolyze in aqueous media at pH 3 at room temperature within one month.

The pH of the present aqueous dental composition is suitably set in view of the application, e.g. etching, but also in view of chemical compatibility with the further components comprised in the composition and/or in the restorative material. Preferably, the aqueous dental composition according to the present invention has a pH of less than 6.5, more preferably pH is from 1 to 6, even more preferably from 2 to 5.

The present invention provides an aqueous dental composition having a pH of at most 7. The aqueous dental composition of the present invention is polymerizable or copolymerizable by a radical polymerization. The aqueous dental composition may be a dental material to be used in the oral cavity. Preferably, the present aqueous dental composition is selected from a dental adhesive composition, a dental bonding agent, a dental primer, a dental infiltrant, a pit and fissure sealant, a dental desensitizing composition, a pulp capping composition, a dental composite, dental glass ionomer cement, a dental cement, a seal and protecting composition for naked tooth necks, and a dental root canal sealer composition.

According to (a), the present aqueous dental composition having a pH of at most 7 comprises a polymerizable compound of the following formula (I). The aqueous dental composition may comprise one or more compounds of formula (I). The aqueous dental composition of the present invention comprises the polymerizable compound(s) of formula (I) in an amount of from 1 to 70 percent by weight based on the total weight of the composition. Preferably, the aqueous dental composition comprises one or more compounds of formula (I) in an amount of from 10 to 60 percent by weight, most preferably 20 to 60 percent by weight based on the total weight of the composition.

The amount of compound of formula (I) may be suitably selected in view of the intended application purpose. For example, a dental adhesive composition may comprise 1 to 70 percent by weight, preferably 5 to 20 percent by weight, based on the total weight of the entire composition of one or more compounds of formula (I). A dental bonding agent may comprise 1 to 70 percent by weight, preferably 5 to 20 percent by weight, based on the total weight of the entire composition of one or more compounds of formula (I). A dental primer may comprise 1 to 70 percent by weight, preferably 5 to 20 percent by weight, based on the total weight of the entire composition of one or more compounds of formula (I). A dental infiltrant may comprise 1 to 70 percent by weight, preferably 5 to 20 percent by weight, based on the total weight of the entire composition of one or more compounds of formula (I). A pit and fissure sealant may comprise 1 to 70 percent by weight, preferably 5 to 20 percent by weight, based on the total weight of the entire composition of one or more compounds of formula (I). A dental desensitizing composition may comprise 1 to 70 percent by weight, preferably 5 to 20 percent by weight, based on the total weight of the entire composition of one or more compounds of formula (I). A pulp capping composition may comprise 1 to 50 percent by weight, preferably 5 to 20 percent by weight, based on the total weight of the entire composition of one or more compounds of formula (I). A dental composite may comprise 1 to 30 percent by weight, preferably 3 to 10 percent by weight, based on the total weight of the entire composition of one or more compounds of formula (I). A dental glass ionomer cement may comprise 1 to 30 percent by weight, preferably 2 to 10 percent by weight, based on the total weight of the entire composition of one or more compounds of formula (I). A dental cement may comprise 1 to 30 percent by weight, preferably 3 to 10 percent by weight, based on the total weight of the entire composition of one or more compounds of formula (I). A seal and protecting composition for naked tooth necks may comprise 1 to 70 percent by weight, preferably 5 to 20 percent by weight, based on the total weight of the entire composition of one or more compounds of formula (I). A dental root canal sealer composition may comprise 1 to 70 percent by weight, preferably 5 to 20 percent by weight, based on the total weight of the entire composition of one or more compounds of formula (I).

An aqueous dental composition comprises a compound according to the following formula (I):

$$A\text{-}L\text{-}B \tag{I}$$

In formula (I), A is a specific polymerizable group which is linked by a divalent linker group L to a group B. The group B may be polymerizable.

According to the present invention, A is a group of the following formula (II)

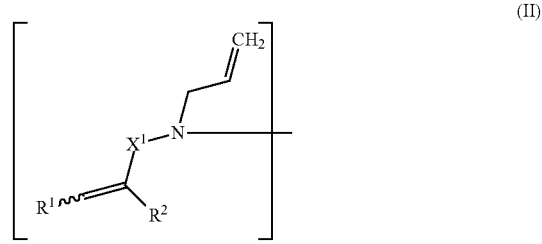

Accordingly, any compound of formula (I) is characterized by an allyl group bonded to a nitrogen atom and a further specific group having a polymerizable double bond which is bonded via $X^1$ to the same nitrogen atom. The specific arrangement of the polymerizable double bond of the allyl group and a further polymerizable double bond which is bonded to the same nitrogen atom activates the allyl bond so that the allyl bond takes part in the radical polymerization reaction during curing.

In formula (II), the jagged bond indicates that $R^1$ may be in cis or trans configuration relative to $X^1$. In formulae (III), (IV) and (VI), the jagged bond has an analogous meaning. In particular, in formula (III), the jagged bond indicates that $R^{1'}$ may be in cis or trans configuration relative to $X^1$. In formula (IV), the jagged bond indicates that $R^{1''}$ may be in cis or trans configuration relative to $X^3$. In formula (VI), the jagged bond indicates that $R^{1*}$ may be in cis or trans configuration relative to $X^{2*}$.

In formula (II), $X^1$ is CO, CS, $CH_2$, or a group $[X'Z]_k$, wherein X' is an oxygen atom, a sulfur atom or NH, Z is a straight chain or branched $C_{1-4}$ alkylene group, and k is an integer of from 1 to 10. Preferably, in formula (II), $X^1$ is CO.

In case $X^1$ is CO, CS, $CH_2$ in formula (II), a polymerizable double bond is present which may take part with the allyl group directly bonded to the nitrogen atom of the group of formula (II) in a cyclopolymerization reaction according to the following Scheme 1.

Scheme 1

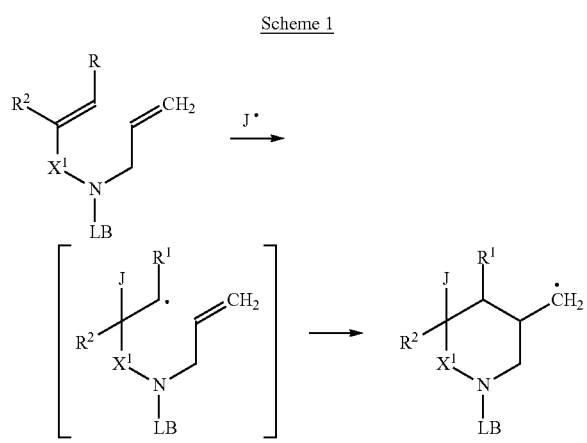

In case $X^1$ is a group $[X'Z]_k$ in formula (II), it is preferred that LB provides a polymerizable double bond which may take part with the allyl group directly bonded to the nitrogen atom of the group of formula (II) in a cyclopolymerization reaction. Preferably, X' is an oxygen atom. Preferred examples for a straight chain or branched $C_{1-4}$ alkylene group for Z are an ethylene group and a propylene group. Preferably, k is an integer of from 1 to 4.

According to a preferred embodiment, in formula (II), $X^1$ is CO.

In formula (II), $R^1$ is a hydrogen atom, —COOM, a straight chain or branched $C_{1-16}$ alkyl group which may be substituted by a $C_{3-6}$ cycloalkyl group, a $C_{6-14}$ aryl or $C_{3-14}$ heteroaryl group, —COOM, —$PO_3M$, —O—$PO_3M_2$ or —$SO_3M$, a $C_{3-6}$ cycloalkyl group which may be substituted by a $C_{1-16}$ alkyl group, a $C_{6-14}$ aryl or $C_{3-14}$ heteroaryl group, —COOM, —$PO_3M$, —O—$PO_3M_2$ or —$SO_3M$, a $C_{6-14}$ aryl or $C_{3-14}$ heteroaryl group which may be substituted by —COOM, —$PO_3M$, —O—$PO_3M_2$ or —$SO_3M$.

For $R^1$ of formula (II), the straight chain or branched $C_{1-16}$ alkyl group may e.g. be methyl, ethyl, n-propyl, i-propyl, n-butyl, isobutyl, tert-butyl, sec-butyl, pentyl or hexyl. An aryl group may, for example, be a phenyl group or a naphthyl group. A $C_{3-14}$ heteroaryl group may contain 1 to 3 heteroatoms selected from nitrogen, oxygen and sulfur.

Preferably, $R^1$ is a hydrogen atom, a straight chain or branched $C_{1-8}$ alkyl group which may be substituted by a $C_{4-6}$ cycloalkyl group, a $C_{6-10}$ aryl or $C_{4-10}$ heteroaryl group, a $C_{4-6}$ cycloalkyl group which may be substituted by a $C_{1-6}$ alkyl group, a $C_{6-10}$ aryl or $C_{4-10}$ heteroaryl group or a $C_{6-10}$ aryl group. More preferably, $R^1$ is a hydrogen atom, a straight chain or branched $C_{1-4}$ alkyl group which may be substituted by a cyclohexyl group or a phenyl group, or a cyclohexyl group which may be substituted by a $C_{1-4}$ alkyl group. Most preferably, $R^1$ is a hydrogen atom.

In formula (II), $R^2$ is a hydrogen atom, —COOM, a straight chain or branched $C_{1-16}$ alkyl group which may be substituted by a $C_{6-14}$ aryl or $C_{3-14}$ heteroaryl group, —COOM, —$PO_3M$, —O—$PO_3M_2$ and —$SO_3M$, a $C_{3-6}$ cycloalkyl group which may be substituted by a $C_{1-16}$ alkyl group, a $C_{6-14}$ aryl or $C_{3-14}$ heteroaryl group, —COOM, —$PO_3M$, —O—$PO_3M_2$ or —$SO_3M$, or a $C_{6-14}$ aryl or $C_{3-14}$ heteroaryl group which may be substituted by —COOM, —$PO_3M$, —O—$PO_3M_2$ and —$SO_3M$.

For $R^2$ of formula (II), the $C_{1-16}$ alkyl group may e.g. be methyl, ethyl, n-propyl, i-propyl, n-butyl, isobutyl, tert-butyl sec-butyl, pentyl or hexyl. An aryl group may, for example, be a phenyl group or a naphthyl group. A $C_{3-14}$ heteroaryl group may contain 1 to 3 heteroatoms selected from nitrogen, oxygen and sulfur.

Preferably, $R^2$ is a hydrogen atom, a straight chain or branched $C_{1-8}$ alkyl group which may be substituted by a $C_{4-6}$ cycloalkyl group, a $C_{6-10}$ aryl, $C_{4-10}$ heteroaryl group or —COOM, a $C_{4-6}$ cycloalkyl group which may be substituted by a $C_{1-6}$ alkyl group, a $C_{6-10}$ aryl, $C_{4-10}$ heteroaryl group or —COOM, or a $C_{6-10}$ aryl group which may be substituted by —COOM. More preferably, $R^2$ is a hydrogen atom, a straight chain or branched $C_1$ alkyl group which may be substituted by a cyclohexyl group, a phenyl group or —COOM, or a cyclohexyl group which may be substituted by a $C_{1-4}$ alkyl group. Even more preferably, $R^2$ a hydrogen atom, a straight chain or branched $C_{1-4}$ alkyl group which may be substituted by —COOM, more preferably a hydrogen atom, a methyl group or —$CH_2$—COOM. Most preferably, $R^2$ is a hydrogen atom.

The following groups are preferred groups of formula (II), wherein M is a hydrogen atom or a metal atom:

(IIa)

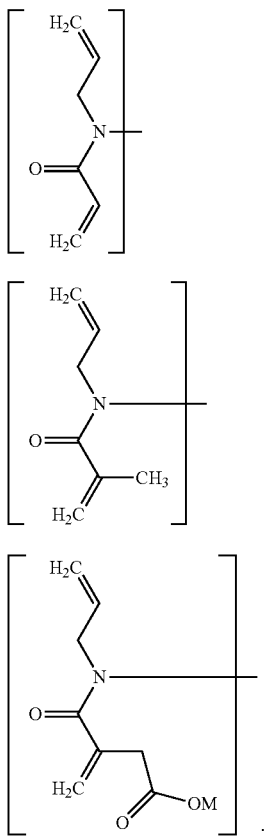

The group of formula (IIb) is particularly preferred.

In formula (I), L is a divalent $C_{2-12}$ alkenylene linker group, which may contain 1 to 3 carbonyl groups or heteroatoms selected from oxygen, nitrogen and sulfur, and which may be substituted by a hydroxyl group, a $C_{6-14}$ aryl group, —COOM, —$PO_3M$, —O—$PO_3M_2$ or —$SO_3M$, wherein M is a hydrogen atom or a metal atom.

For L of formula (I), specific examples of a divalent $C_{2-12}$ alkenylene linker group are straight chain or branched $C_{2-12}$ alkenylene groups such as ethenylene, propenylene, butenylene, pentenylene or hexenylene, or cyclic $C_{3-12}$ alkenylene groups such as cyclopropenylene, cyclobutenylene, cyclopentenylene, cyclohexenylene. Preferably, divalent linker group L is a straight chain or branched $C_{2-12}$ alkenylene group.

It is preferred that divalent linker group L is a straight chain $C_{2-8}$ alkenylene linker group, which may optionally include one or more —CO— group. More preferably, a divalent linker group L is —$CH_2$—CH=CH—$CH_2$— or —CO—CH=CH—CO—. The substituents of the C—C double bond are preferably in trans configuration. Most preferably, L is —$CH_2$—CH=CH—$CH_2$— in trans configuration.

In formula (I), B is selected from (i) a group according to the definition of A, (ii) a group of the following formula (III), (iii) a group of the following formula (IV) and (iv) a group of the formula $[Z'X'']_mE$.

When B is a group according to formula (II) in the definition of A, then B may be the same or different from the group A present in a polymerizable compound of formula (I). Specifically, B may be a group of the above formula (II) wherein an allyl group is bonded to a nitrogen atom, and a further group having a polymerizable double bond is bonded to the same nitrogen atom.

When B is a group according to formula (II) in the definition of A, $X^1$ is CO, CS, $CH_2$, or a group $[X'Z]_k$, wherein X' is an oxygen atom, a sulfur atom or NH, Z is a straight chain or branched $C_1$ alkylene group, and k is an integer of from 1 to 10.

According to a preferred embodiment of B being a group according to formula (II) in the definition of A, $X^1$ is CO.

When B is a group according to formula (II) in the definition of A, $R^1$ independently has the same meaning as defined above for formula (II).

When B is a group according to formula (II) in the definition of A, $R^2$ independently has the same meaning as defined above for formula (II).

When B is a group of the formula (III), B is as follows:

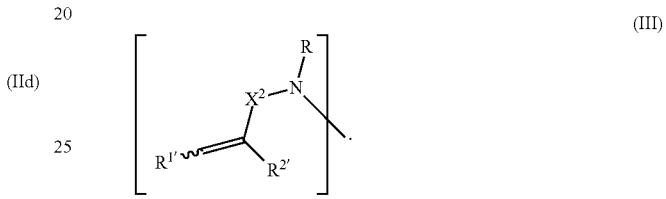

In formula (III), $X^2$ has the same meaning as defined for $X^1$ in formula (II). Specifically, when B is a group according to formula (III), $X^2$ is CO, CS, $CH_2$, or a group $[X'Z]_k$, wherein X' is an oxygen atom, a sulfur atom or NH, Z is a straight chain or branched $C_{1-4}$ alkylene group, and k is an integer of from 1 to 10. X', Z and k of a group of formula (III) maybe the same or different of X', Z and k of group of formula (II) present as A in the polymerizable compound of formula (I).

Preferably, in formula (III), X' is an oxygen atom. Preferred examples for a straight chain or branched $C_{1-4}$ alkylene group for Z are an ethylene group and a propylene group. Preferably, k is an integer of from 1 to 4.

In formula (III), $R^1$ and $R^2$ are independent from each other and independently have the same meaning as defined for $R^1$ and $R^2$ in formula (II).

Specifically, when B is a group according to formula (III), $R^1$ is a hydrogen atom, —COOM, a straight chain or branched $C_{1-6}$ alkyl group which may be substituted by a $C_{3-6}$ cycloalkyl group, a $C_{6-14}$ aryl or $C_{3-14}$ heteroaryl group, —COOM, —$PO_3M$, —O—$PO_3M_2$ or —$SO_3M$, a $C_{3-6}$ cycloalkyl group which may be substituted by a $C_{1-16}$ alkyl group, a $C_{6-14}$ aryl or $C_{3-14}$ heteroaryl group, —COOM, —$PO_3M$, —O—$PO_3M_2$ or —$SO_3M$, a $C_{6-14}$ aryl or $C_{3-14}$ heteroaryl group which may be substituted by —COOM, —$PO_3M$, —O—$PO_3M_2$ or —$SO_3M$.

According to a preferred embodiment when B is a group according to formula (III), $R^{1'}$ is a hydrogen atom. In case $R^{1'}$ is a $C_{1-6}$ alkyl group, the $C_{1-6}$ alkyl group is preferably substituted by —COOM.

When B is a group according to formula (III), $R^{2'}$ is a hydrogen atom, —COOM, a straight chain or branched $C_{1-6}$ alkyl group which may be substituted by a $C_{6-14}$ aryl or $C_{3-14}$ heteroaryl group, —COOM, —$PO_3M$, —O—$PO_3M_2$ and —$SO_3M$, a $C_{3-6}$ cycloalkyl group which may be substituted by a $C_{1-6}$ alkyl group, a $C_{1-4}$ aryl or $C_{3-14}$ heteroaryl group, —COOM, —$PO_3M$, —O—$PO_3M_2$ or —$SO_3M$, or a $C_{6-14}$ aryl or $C_{3-14}$ heteroaryl group which may be substituted by —COOM, —$PO_3M$, —O—$PO_3M_2$ and —$SO_3M$, According to a preferred embodiment of B being a group according to formula (III), $R^{2'}$ is a hydrogen atom or a straight chain or branched $C_{1-6}$ alkyl group, more preferably a hydrogen atom or a straight chain or branched $C_{1-4}$ alkyl group, most preferably a hydrogen group or a methyl group.

In formula (III), R is a hydrogen atom, a straight chain or branched $C_{1-16}$ alkyl group which may be substituted by a $C_{3-6}$ cycloalkyl group, a $C_{6-14}$ aryl or $C_{3-14}$ heteroaryl group, —COOM, —PO$_3$M, —O—PO$_3$M$_2$ or —SO$_3$M, a $C_{3-6}$ cycloalkyl group which may be substituted by a $C_{1-16}$ alkyl group, a $C_{6-14}$ aryl or $C_{3-14}$ heteroaryl group, —COOM, —PO$_3$M, —O—PO$_3$M$_2$ or —SO$_3$M, a $C_{6-14}$ aryl group which may be substituted by —COOM, —PO$_3$M, —O—PO$_3$M$_2$ or —SO$_3$M.

Preferably, R is a hydrogen atom, a straight chain or branched $C_{1-8}$ alkyl group which may be substituted by a $C_{4-6}$ cycloalkyl group, a $C_{6-10}$ aryl or $C_{4-10}$ heteroaryl group, a $C_{4-6}$ cycloalkyl group which may be substituted by a $C_{1-6}$ alkyl group, a $C_{6-10}$ aryl or $C_{4-10}$ heteroaryl group or a $C_{6-10}$ aryl group. More preferably, R is a hydrogen atom, a straight chain or branched $C_{1-4}$ alkyl group which may be substituted by a cyclohexyl group or a phenyl group, or a cyclohexyl group which may be substituted by a $C_{1-4}$ alkyl group. Most preferably, R is a hydrogen atom, methyl, ethyl, cyclohexyl or benzyl.

Preferred groups of B of the formula (III) are as follows wherein M is a hydrogen atom or a metal atom:

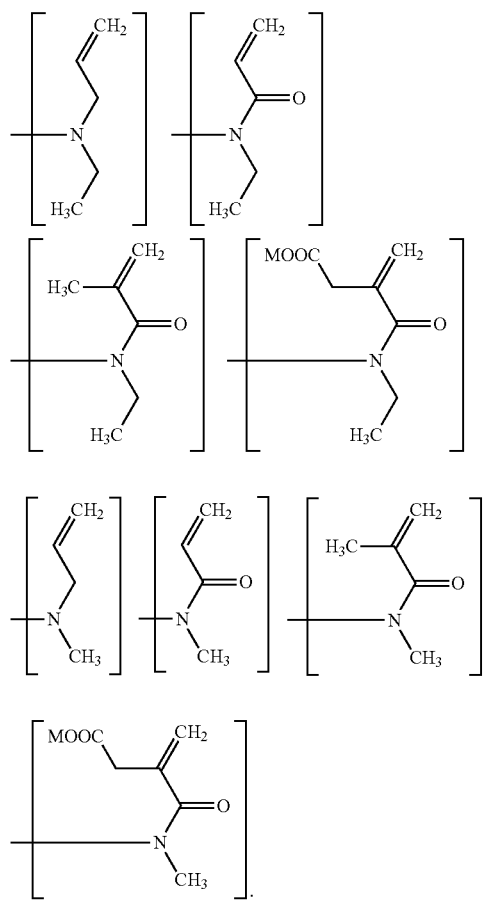

When B is a group of the formula (IV), B is as follows:

In formula (IV), $X^3$ is CO, —CH$_2$CO—, CS or —CH$_2$CS—, According to a preferred embodiment, $X^3$ is CO or —CH$_2$CO—.

In formula (IV), $R^{1'''}$ and $R^{2'''}$ are independent from each other and independently have the same meaning as defined for $R^1$ and $R^2$ in formula (II).

Specifically, when B is a group according to formula (IV), $R^{1'''}$ is a hydrogen atom, —COOM, a straight chain or branched $C_{1-16}$ alkyl group which may be substituted by a $C_{3-6}$ cycloalkyl group, a $C_{6-14}$ aryl or $C_{3-14}$ heteroaryl group, —COOM, —PO$_3$M, —O—PO$_3$M$_2$ or —SO$_3$M, a $C_{3-6}$ cycloalkyl group which may be substituted by a $C_{1-16}$ alkyl group, a $C_{6-14}$ aryl or $C_{3-14}$ heteroaryl group, —COOM, —PO$_3$M, —O—PO$_3$M$_2$ or —SO$_3$M, a $C_{6-14}$ aryl or $C_{3-14}$ heteroaryl group which may be substituted by —COOM, —PO$_3$M, —O—PO$_3$M$_2$ or —SO$_3$M.

According to a preferred embodiment when B is a group according to formula (IV), $R^{1'''}$ is a hydrogen atom. In case $R^{1'''}$ is a $C_{1-16}$ alkyl group, the $C_{1-16}$ alkyl group is preferably substituted by —COOM.

When B is a group according to formula (IV), $R^{2'''}$ is a hydrogen atom, —COOM, a straight chain or branched $C_{1-16}$ alkyl group which may be substituted by a $C_{6-14}$ aryl or $C_{3-14}$ heteroaryl group, —COOM, —PO$_3$M, —O—PO$_3$M$_2$ and —SO$_3$M, a $C_{3-6}$ cycloalkyl group which may be substituted by a $C_{1-16}$ alkyl group, a $C_{6-14}$ aryl or $C_{3-14}$ heteroaryl group, —COOM, —PO$_3$M, —O—PO$_3$M$_2$ or —SO$_3$M, or a $C_{6-14}$ aryl group which may be substituted by —COOM, —PO$_3$M, —O—PO$_3$M$_2$ and —SO$_3$M, According to a preferred embodiment of B being a group according to formula (IV), $R^{2'''}$ is a hydrogen atom or a methyl group.

Preferred groups of formula (IV) are selected from the group consisting of:

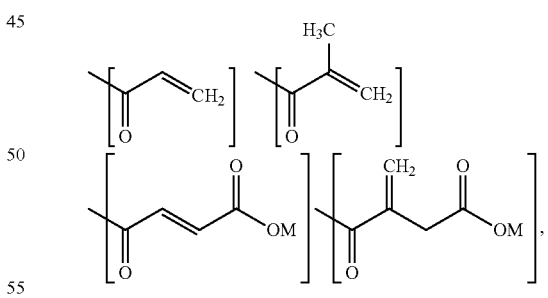

wherein M is a hydrogen atom or a metal atom.

According to the definition of the present invention, the M which are independent from each other, each represent a hydrogen atom or a metal atom. The metal atom is preferably an alkali metal or an alkaline earth metal. Specific examples of the alkali metal are lithium, sodium, and potassium. Specific examples of the alkaline earth metal are calcium, strontium and magnesium. The metal atom may also be tin.

When B is a group [Z'X'']$_m$E, the meaning of Z', X'', m, and E is as follows. Z' is a straight chain or branched $C_{1-4}$ alkylene group. Specific examples of the $C_{1-4}$ alkylene groups are methylene, ethylene, propylene and butylene. X" is an oxygen atom, a sulfur atom or NH.

E is a hydrogen atom, $PO_3M_2$, a straight chain or branched $C_{1-16}$ alkyl group which may be substituted by a $C_{3-6}$ cycloalkyl group, a $C_{6-14}$ aryl or $C_{3-14}$ heteroaryl group, —COOM, —$PO_3M$, —O—$PO_3M_2$ or —$SO_3M$, a $C_{3-6}$ cycloalkyl group which may be substituted by a $C_{1-16}$ alkyl group, a $C_{6-14}$ aryl or $C_{3-14}$ heteroaryl group, —COOM, —$PO_3M$, —O—$PO_3M_2$ or —$SO_3M$, a $C_{6-14}$ aryl or $C_{3-14}$ heteroaryl group which may be substituted by —COOM, —$PO_3M$, —O—$PO_3M_2$ or —$SO_3M$.

In formula group $[Z'X'']_mE$, m is an integer of from 1 to 10.

According to a preferred embodiment, B is (i) a group according to the definition of A. According to a particularly preferred embodiment, compound of formula (I) is N,N'-diallyl-1,4-bisacrylamido-(2E)-but-2-en (BAABE) having the following structural formula:

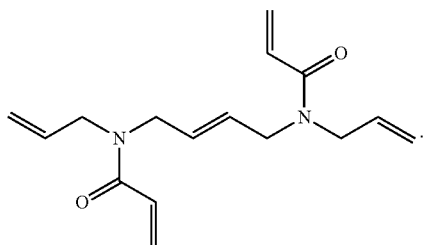 [SMILES: C=CCN(C/C=C/CN(CC=C)C(=O)C=C)C(=O)C=C]

The polymerizable compound of formula (I) may be prepared according to the following Scheme 2, wherein A and B represent polymerizable groups, and C and G represent groups which are suitable for providing a linkage between A and L and L and B respectively, as shown in the following Scheme 2:

A-C+G-L-G+C—B → A-L-B   Scheme 2

The linkage may be formed by a substitution reaction, an addition reaction or a condensation reaction. The reaction may involve the formation of an amine bond, an amide bond or an urethane bond. Preferably, the reaction is a substitution reaction and involves the formation of an amine bond.

The polymerizable compound of formula (I) may be prepared by a reaction wherein a stoichiometric mixture of compound A-C and G-L-G is reacted and then the reaction product is reacted with a compound C—B. Alternatively, it is possible to prepare a polymerizable compound of formula (I) by a reaction wherein a mixture of compound B—C and G-L-G is reacted first, and then the reaction product is reacted with compound A-C. Or, according to a particularly preferred alternative, A-C and C—B are identical compounds, wherein about two molar equivalents of these compounds are reacted with one molar equivalent of G-L-G. Depending on the nature of A and B, further reaction steps may be required in order to arrive at the above defined groups A and B, or A and B are identical with A and B.

An exemplary pathway for the preparation of N,N'-diallyl-1,4-bisacrylamido-(2E)-but-2-en (BAABE) is depicted in the following Scheme 3:

Scheme 3

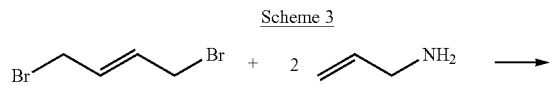

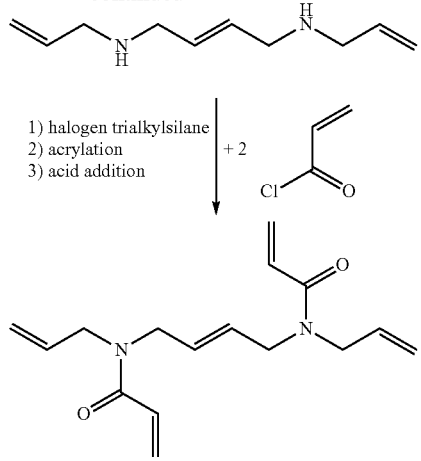

The reaction may be performed in accordance with, for example, the methods described in Jerry March "Advanced Organic Chemistry" $6^{th}$ Edition, John Wiley & Sons, INC., 2007 and Richard C. Larock "Comprehensive Organic Transformation", VCH Publishers, INC., 2010, $2^{nd}$ revised edition, or a method conforming to the methods described above. The reaction may be carried out in a solvent which is capable of dissolving the reactants. For the first step of reacting 1,4-dibromo-2-butene with allylamine, a suitable solvent is e.g. acetonitrile. For the second step of reacting the product of step 1 with acryloyl chloride, a suitable solvent is e.g. dichloromethane. For the second step, a suitable halogen trialkylsilane is chlorotrimethylsilane, wherein a suitable organic base such as triethylamine is added and optionally an antioxidant such as 2,6-di-tert-butyl-methylphenol is added for stabilization. After acrylation with acryloyl chloride, a suitable acid such as hydrochloric acid is added.

According to (b), the present aqueous dental composition having a pH of at most 7 comprises a polymerizable compound of the following formula (V). The aqueous dental composition may comprise one or more compounds of formula (V). The aqueous dental composition of the present invention comprises the polymerizable compound(s) of formula (V) in an amount of from 2 to 20 percent by weight based on the total weight of the composition. Preferably, the aqueous dental composition comprises one or more compounds of formula (V) in an amount of from 3 to 15 percent by weight, most preferably 4 to 10 percent by weight based on the total weight of the composition.

A compound of formula (V) is according to the following formula (V):

A'-L'-A'   (V).

In formula (V), A' is a specific polymerizable group which is linked by divalent linker group L' to a group A' which is the same or different polymerizable group as the first mentioned polymerizable group A'.

According to the present invention, A' is a group of the following formula (VI)

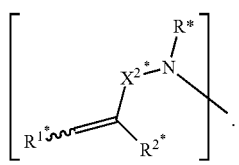
(VI)

Accordingly, any compound of formula (V) is characterized by a group of formula (VI) having a polymerizable double bond which is bonded to the nitrogen atom via $X^2$.

In formula (VI), $R^{1*}$ and $R^{2*}$ are independent from each other and independently have the same meaning as defined for $R^1$ and $R^2$ in above formula (II). Furthermore, $X^{2*}$ and $R^*$ independently have the same meaning as defined for $X^2$ and R in above formula (III).

In formula (VI), L' is a divalent $C_{2-12}$ alkylene linker group, which may contain 1 to 3 carbonyl groups or heteroatoms selected from oxygen, nitrogen and sulfur, and which may be substituted by a hydroxyl group, a $C_{6-14}$ aryl group, —COOM, —$PO_3M$, —O—$PO_3M_2$ or —$SO_3M$, wherein M is a hydrogen atom or a metal atom.

For L' of formula (VI), specific examples of a divalent $C_{2-12}$ alkylene linker group are straight chain or branched $C_{2-12}$ alkylene groups such as ethylene, propylene, butylene, pentylene or hexylene, or cyclic $C_{3-12}$ alkylene groups such as cyclopropylene, cyclobutylene, cyclopentylene, cyclohexylene. Preferably, divalent linker group L' is a straight chain or branched $C_{2-12}$ alkylene group.

It is preferred that divalent linker group L' is —$(CH_2)_{2-8}$— or —CO—$(CH_2)_{2-8}$—CO—. More preferably, divalent linker group L' is —$(CH_2)_3$— or —CO—CH—CO—, most preferably n-propylene.

In contrast to formula (II), for formula (VI), the particular preferred selection for $R^{2*}$ differs from that for $R^2$ of formula (II) in that it is particularly preferred that $R^{2*}$ is a hydrogen atom.

For example, compounds of formula (V) may be bisacrylamide compounds having the following structural formulae:

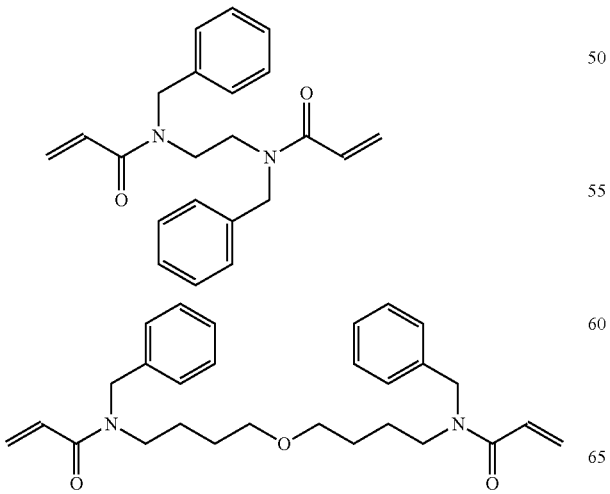

or bismethacrylamide compounds having the following structural formulae:

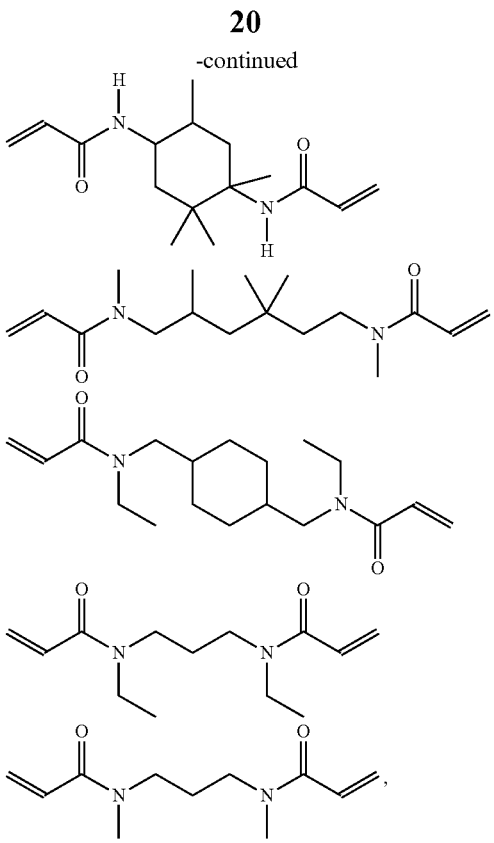

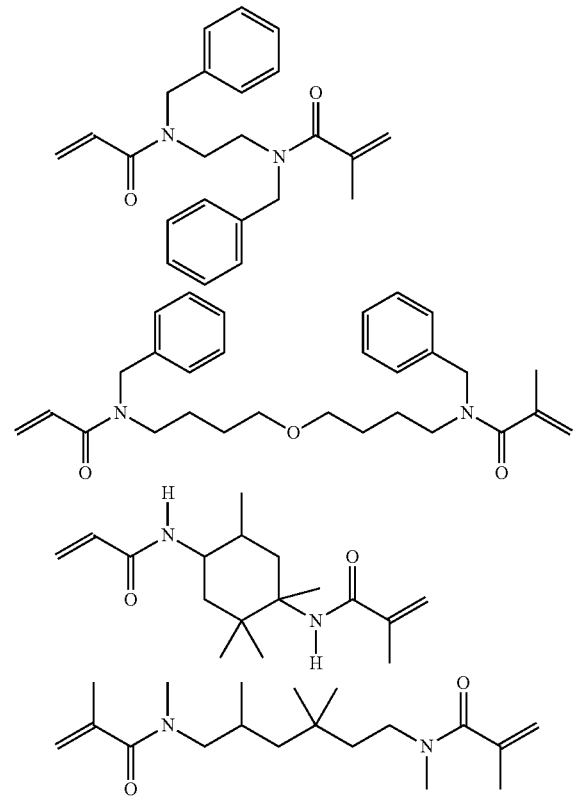

-continued

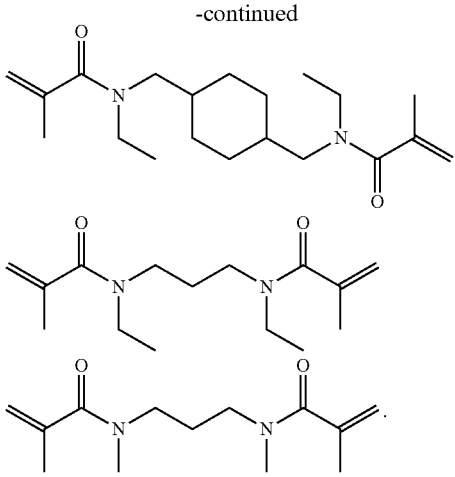

According to a preferred embodiment, in formula (VI), for $X^{2*}$, $R^{1*}$, $R^{2*}$ and $R^{2*}$, at least one of the following features is selected:
$X^{2*}$ is CO,
R* is an ethyl group,
$R^{1*}$ is a hydrogen atom,
$R^{2*}$ is a hydrogen atom.

According to a particularly preferred embodiment, compound of formula (V) is N,N'-diethyl-1,3-bisacrylamidopropan (BADEP).

The polymerizable compound of formula (V) may be prepared in an analogous way as explained for compound of formula (I) above.

The specific combination of compounds of formulae (I) and (V) provides for a synergistically improvement of both wetting of a dental surface by the aqueous dental composition and viscosity of the aqueous dental composition. This in turn results in a simplified and facilitated application of the aqueous dental composition on a dental surface. In addition, the penetration of the dental surface is improved.

Furthermore, owing to the specific combination of compounds of formulae (I) and (V), both the uncured and the cured dental composition provides for an improved stability. This is because compounds of formulae (I) and (V) do not comprise groups being susceptible to cleavage under acidic conditions.

According to (c), the aqueous dental composition comprises a polymerizable monomer having one or more acidic groups. The aqueous dental composition may comprise one or more polymerizable monomer(s) having one or more acidic groups. The aqueous dental composition of the present invention comprises the polymerizable monomer(s) having one or more acidic groups in an amount of from 1 to 20 percent by weight based on the total weight of the composition. Preferably, the aqueous dental composition comprises one or more polymerizable monomer(s) having one or more acidic groups in an amount of from 4 to 19 percent by weight, most preferably 8 to 18 percent by weight based on the total weight of the composition.

The polymerizable monomer having one or more acidic groups preferably has a group imparting acidity to said monomer. More preferably, the acidic group is selected from the group consisting of a phosphoric acid ester group, a phosphonic acid group, a sulfonic acid group and a carboxylic acid group.

Furthermore, the polymerizable monomer having one or more acidic groups has at least one polymerizable double bond. The polymerizable monomer having one or more acidic groups may be selected from the group of the following compounds (IX), (X) and (XI).

Phosphoric acid ester group containing polymerizable compounds having at least one polymerizable double bond preferably have the following formula (IX):

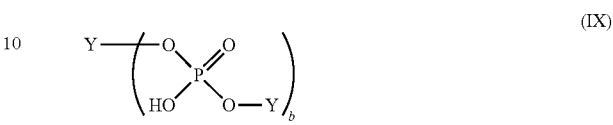

wherein
the moieties Y independent from each other represent a hydrogen atom or a moiety of the following formulae (Y*), (Y) or (Y*):

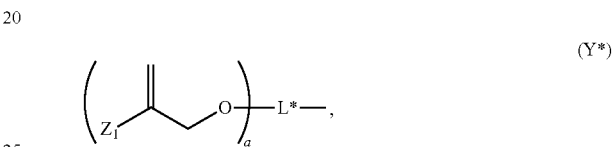

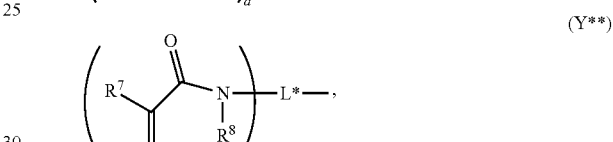

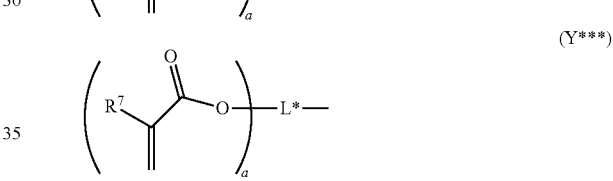

wherein
$Z_1$ is $COOR^5$, $COSR^6$, $CON(R^5)_2$, $CONR^5R^6$, or $CONHR^5$, wherein $R^5$ and $R^6$ independently represent a hydrogen atom, a $C_{1-18}$ alkyl group optionally substituted by a $C_{3-8}$ cycloalkyl group, an optionally substituted $C_{3-8}$ cycloalkyl group, an optionally substituted $C_{4-18}$ aryl or heteroaryl group, an optionally substituted $C_{5-18}$ alkylaryl or alkylheteroaryl group, or an optionally substituted $C_{7-30}$ aralkyl group, whereby two $R^5$ residues may form together with the adjacent nitrogen atom to which they are bound a 5- to 7-membered heterocyclic ring which may contain further nitrogen atoms or an oxygen atoms, and whereby the optionally substituted groups may be substituted by 1 to 5 Cis alkyl group(s);

$R^7$ and $R^8$ independently represent a hydrogen atom, an optionally substituted $C_{1-8}$ alkyl group, an optionally substituted $C_{3-18}$ cycloalkyl group, an optionally substituted $C_{5-18}$ aryl or heteroaryl group, an optionally substituted $C_{5-18}$ alkylaryl or alkylheteroaryl group, an optionally substituted $C_{7-30}$ aralkyl group, whereby the optionally substituted groups may be substituted by 1 to 5 $C_{1-5}$ alkyl group(s);

L* represents an (a+b)-valent organic residue (whereby b is 1 when Y in formula (IX) is within the round brackets) containing 2 to 45 carbon atoms and optionally heteroatoms such as oxygen, nitrogen and sulfur atoms, the carbon atoms including a+b carbon atoms selected from primary and secondary aliphatic carbon atoms, secondary alicyclic carbon atoms, and aromatic carbon atoms, each of the a+b carbon atoms linking a phosphate or a moiety of any one of formula (Y*), (Y) and (Y*); a is an integer of from 1 to 10, preferably 1 to 5; b is an integer of from 1 to 10, preferably 1 to 5; provided that at least one Y is not hydrogen. The preparation of such compounds wherein Y=Y* is known from EP-A 1 548 021.

Furthermore, the polymerizable monomer having one or more acidic groups may be selected from:
1) phosphonic acid group containing polymerisable acidic compounds of the following formula (X):

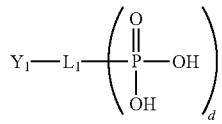
(X)

wherein
the moiety $Y_1$ represents a moiety of the following formulae $(Y_1^*)$, $(Y_1^{})$ or $(Y_1^{*})$:

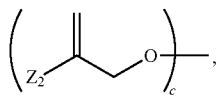
$(Y_1^*)$

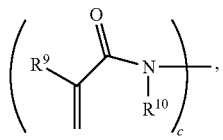
$(Y_1^{**})$

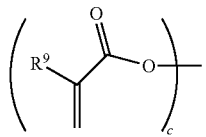
$(Y_1^{***})$ $Z_2$ independently has the same meaning as defined for $Z_1$;
$R^9$ and $R^{10}$ independently have the same meaning as defined for $R^7$ and $R^8$;
$L_1$ represents a (c+d) valent organic residue containing 2 to 45 carbon atoms and optionally heteroatoms such as oxygen, nitrogen and sulfur, the carbon atoms including c+d carbon atoms selected from primary and secondary aliphatic carbon atoms, secondary alicyclic carbon atoms, and aromatic carbon atoms, each of the c+d carbon atoms linking a phosphonate or a moiety of any one of formula $(Y_1^*)$, $(Y_1^{})$ and $(Y_1^{*})$; and c and d independently represent integers of from 1 to 10; and/or
2) sulfonic acid group containing polymerisable acidic compounds of the following formula (XI):

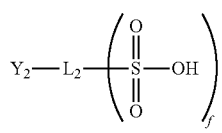
(XI)

wherein
the moiety $Y_2$ represents a moiety of the following formulae $(Y_2^*)$, $(Y_2^{})$ or $(Y_2^{*})$:

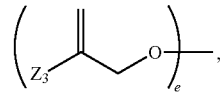
$(Y_2^*)$

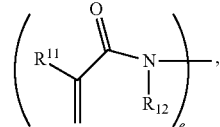
$(Y_2^{**})$

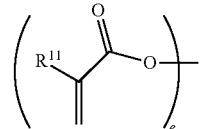
$(Y_2^{***})$ $Z_3$ independently has the same meaning as defined for $Z_1$.

$R^{11}$ and $R^{12}$ independently have the same meaning as defined for $R^7$ and $R^8$;

$L_2$ represents an (e+f) valent organic residue containing 2 to 45 carbon atoms and optionally heteroatoms such as oxygen, nitrogen and sulfur atoms, the carbon atoms including e+f carbon atoms selected from primary and secondary aliphatic carbon atoms, secondary alicyclic carbon atoms, and aromatic carbon atoms, each of the e+f carbon atoms linking a sulphonate or a moiety of any one of formula $(Y_2^*)$, $(Y_2^{})$ and $(Y_2^{*})$; and e and f independently represent an integer of from 1 to 10.

It is preferred to select compounds of formula (IX), (X) and (XI) with the proviso that they do not contain ester groups, or at least only ester groups which do not hydrolyze in aqueous media at pH 3 at room temperature within one month, such as the phosphoric acid ester group of compounds of formula (IX). Thereby, an advantageous stability of the aqueous dental composition having a pH of at most 7 in terms of shelf-life stability of the uncured dental composition as well as stability after curing in the mouth of a patient is ensured. Therefore, particularly preferred are compounds of formula (IX) excluding the moiety of formula Y*** and the moiety of formula Y* wherein $Z_1$ is COOR$^5$ or COSR$^6$, compounds of formula (X) excluding the moiety of formula $Y_1^{***}$ and the moiety of formula $Y_1^*$ wherein $Z_2$ is COOR$^5$ or COSR$^6$ as well as compounds of formula (XI) excluding the moiety of formula $Y_2^{***}$ and the moiety of formula $Y_2^*$ wherein $Z_3$ is COOR$^5$ or COSR$^6$.

Carboxylic acid group containing polymerizable compounds having at least one polymerizable double bond may be selected e.g. from acrylic acid and methacrylic acid.

From the phosphoric acid ester group containing polymerizable compound having at least one polymerizable double bond, compounds of formula (IX') characterized by one of the following formulae are particularly preferred:

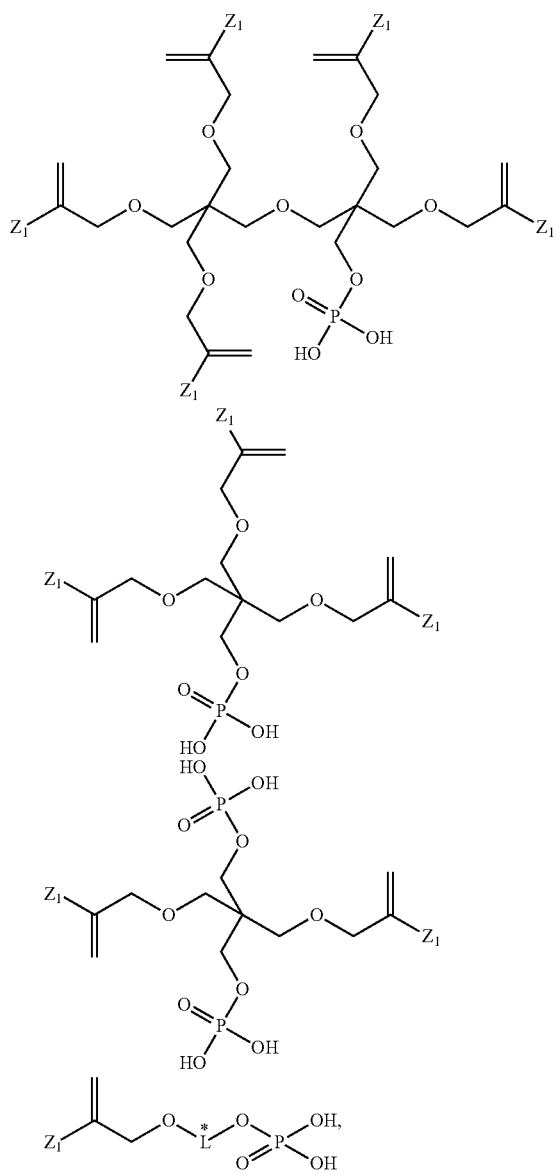

wherein $Z_1$ is defined as above, and L* is an optionally substituted alkylene group. More preferably, $Z_1$ is methyl, and L* is a $C_4$ to $C_{16}$ alkylene group. Even more preferably, L* is a $C_8$ to $C_{12}$ alkylene group.

From the sulfonic acid group containing polymerizable compound having at least one polymerizable double bond, compounds of formula (XI') characterized by one of the following formulae are particularly preferred:

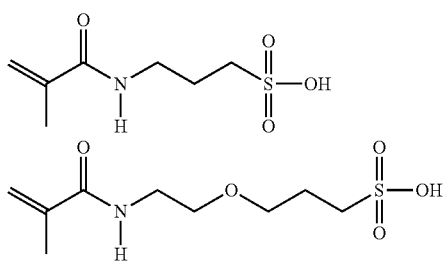

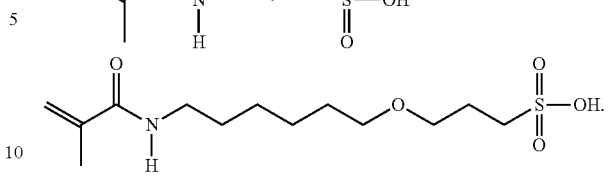

In a preferred embodiment, according to (c), the polymerizable monomer having one or more acidic groups is a polymerizable phosphoric acid ester according to formula (IX).

According to (d), the aqueous dental composition comprises a photoinitiator system.

The term "polymerization initiator system" refers to a system comprising at least a 1,2-diketone photoinitiator compound.

Preferably, the polymerization initiator system comprises:
(d-i) an 1,2-diketone photoinitiator compound having a light absorption maximum in the range from 300 to 500 nm;
(d-ii) optionally a coinitiator compound; and
(d-iii) optionally a polymerization initiator auxiliary substance.

The photoinitiator system may comprise one or more of any one of components (d-i), (d-ii) and (d-iii).

The term "1,2-diketone photoinitiator" denotes any chemical compound having 1,2-diketone functional group, which compound forms free radicals when activated, e. g. by exposure to light or interaction with a coinitiator and optionally a polymerization initiator auxiliary substance in a photochemical process.

1,2-diketone photoinitiator according to (d-i) belongs to the Norrish type I photoinitiators which provide free radical intermediates by photochemical abstraction. Preferably, the 1,2-diketone photoinitiator compound according to (d-i) is selected from the group consisting of camphorquinone, benzil, 2,2'-3 3'- and 4,4'-dihydroxylbenzil, 2,3-butanedione, 2,3-pentanedione, 2,3-hexanedione, 3,4-hexanedione, 2,3-heptanedione, 3,4-heptanedione, 2,3-octanedione, 4,5-octanedionefuril, biacetyl, 1,2-cyclohexanedione, 1,2-naphthaquinone and acenaphthaquinone.

The term "coinitiator" as used herein means an electron donor compound, i.e. a compound capable of donating electrons in a photochemical process. Suitable examples include organic compounds having heteroatoms with electron lone pairs, for example amine compounds.

The optional coinitiator compound according to (d-ii) is preferably an electron donor which may be selected from the group consisting of amines, amides, ethers, thioethers, ureas, thioureas, ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid. Particularly preferred electron donors contain an electron donor atom such as a nitrogen, oxygen, phosphorus, or sulfur atom, and an abstractable hydrogen atom bonded to a carbon or silicon atom alpha to the electron donor atom.

More preferably, the coinitiator is an amine compound, even more preferably a tertiary amine selected from the group consisting of triethanolamine, 4-N,N-dimethylaminobenzonitrile, methyl N,N-dimethylaminobenzoate, ethyl N,N-dimethylaminobenzoate, N,N-dimethylaminoethyl methacrylate and isoamyl 4-N,N-dimethylaminobenzoate, N,N-dimethylaniline, N,N-dimethyltoluidine, N,N-diethanoltoluidine, dimethylaminoanisole, 1 or 2-dimethylaminonaphthalene. In particular, the tertiary amine is selected from the group consisting of triethanolamine, methyl 4-N,N-dimethylaminobenzoate, ethyl 4-N,N-dimethylaminobenzoate, 4-N,N-dimethylaminoethyl methacrylate and iso-amyl 4-N,N-dimethylaminobenzoate.

Furthermore, the photoinitiator system may additionally comprise (d-iii) a polymerization initiator auxiliary substance which is preferably selected from the group consisting of iodonium-, sulfonium-, phosphonium-, pyridinium salts and aromatic tertiary phosphine compounds.

The term "polymerization initiator auxiliary substance" refers to a molecule that produces an advantageous chemical change in any of the components of the polymerization initiator system in a photochemical process. For example, the polymerization initiator auxiliary substance may be selected from the group consisting of iodonium-, sulfonium-, phosphonium-, pyridinium-salts and aromatic tertiary phosphine compounds.

Iodonium-, sulfonium- or phosphonium-salts are preferably selected from the following group:

(1) an iodonium compound of the following formula (XII):

$$R^{13}-I^+-R^{14}A^- \quad (XII)$$

wherein
R$^{13}$ and R$^{14}$
which are independent from each other represent an organic moiety, and
A$^-$ is an anion;

(2) a sulfonium compound of the following formula (XIII):

$$R^{15}R^{16}R^{17}S^+A^- \quad (XIII)$$

wherein
R$^{15}$, R$^{16}$ and R$^{17}$
which are independent from each other, represent an organic moiety or wherein any two of R$^{15}$, R$^{16}$ and R$^{17}$ form a cyclic structure together with the sulfur atom to which they are bound, and
A$^-$ is an anion;

(3) a phosphonium compound of the following formula (XIV):

$$R^{18}R^{19}R^{20}P^+A^- \quad (XIV)$$

wherein
R$^{18}$, R$^{19}$ and R$^{20}$
which are independent from each other, represent an organic moiety, and
A$^-$ is an anion; and (4) a pyridinium salt.

In the iodonium compounds of formula (XII), R$^{13}$ and R$^{14}$ preferably represent an aromatic, an aliphatic or an alicyclic group. An aromatic group may be a phenyl group. The phenyl group may be substituted by one or more straight chain or branched alkyl groups having 1 to 6 carbon atoms, straight chain or branched alkoxy groups having 1 to 6 carbon atoms, aromatic groups such as aryl groups or aryloxy groups, alicyclic groups having 3 to 6 carbon atoms, halogen atoms, hydroxyl groups, or amino groups. The aliphatic group may be a straight chain or branched alkyl groups having 1 to 6 carbon atoms which may be substituted by one or more aromatic groups, alicyclic groups having 3 to 6 carbon atoms, halogen atoms, hydroxyl groups or amino groups. An alicyclic group may be a group having 3 to 6 carbon atoms which may be substituted by one or more aromatic groups, aliphatic groups, halogen atoms, hydroxyl groups or amino groups.

According to a preferred embodiment, the iodonium compound of formula (XII) is a diaryl iodonium salt. Examples of useful diary iodonium salt include (4-methylphenyl)[4-(2-methylpropyl) phenyl] iodonium hexafluoroantimonate, include (4-methylphenyl)[4-(2-methylpropyl) phenyl] iodonium tetrafluoroborate, diphenyliodonium (DPI) tetrafluoroborate, di(4-methylphenyl)iodonium (Me2-DPI) tetrafluoroborate, phenyl-4-methylphenyliodonium tetrafluoroborate, di(4-heptylphenyl)iodonium tetrafluoroborate, di(3-nitrophenyl)iodonium hexafluorophosphate, di(4-chlorophenyl)iodonium hexafluorophosphate, di(naphthyl)iodonium tetrafluoroborate, di(4-trifluoromethylphenyl)iodonium tetrafluoroborate, DPI hexafluorophosphate, Me2-DPI hexafluorophosphate; DPI hexafluoroarsenate, di(4-phenoxyphenyl)iodonium tetrafluoroborat, phenyl-2-thienyliodonium hexafluorophosphate, 3,5-dimethylpyrazolyl-4-phenyliodonium hexafluorophosphate, DPI hexafluoroantimonate, 2,2'-DPI tetrafluoroborate, di(2,4-dichlorophenyl)iodonium hexafluorophosphate, di(4-bromophenyl)iodonium hexafluorophosphate, di(4-methoxyphenyl)iodonium hexafluorophosphate, di(3-carboxyphenyl) iodonium hexafluorophosphate, di(3-methoxycarbonylphenyl)iodonium hexafluorophosphate, di(3-methoxysulfonylphenyl)iodonium hexafluorophosphate, di(4-acetamidophenyl)iodonium hexafluorophosphate, di(2-benzothienyl)iodonium hexafluorophosphate, and DPI hexafluorophosphate.

Particularly preferred iodonium compounds of formula (XII) include diaryliodonium hexafluorophosphate such as diphenyliodonium (DPI) hexafluorophosphate, di(4-methylphenyl)iodonium (Me2-DPI) hexafluorophosphate, diaryliodonium hexafluoroantimonate, (4-methylphenyl)[4-(2-methylpropyl) phenyl] iodonium hexafluoroantimonate, (4-methylphenyl)[4-(2-methylpropyl)phenyl]iodonium hexafluorophosphate (Irgacure® 250, commercial product available from BASF SE), (4-methylphenyl)[4-(2-methylpropyl) phenyl] iodonium tetrafluoroborate, 4-octyloxyphenyl phenyliodonium hexafluoroantimonate, 4-(2-hydroxytetradecyloxyphenyl)phenyliodonium hexafluoroantimonate, and 4-(1-methylethyl)phenyl 4-methylphenyliodonium tetrakis(pentafluorophenyl)borate.

A preferred sulfonium compound of the formula (XIII) is S-(phenyl)thianthrenium hexafluorophosphate of the following formula:

The phosphonium compound of formula (XIV) may be a tetrakis-(hydroxymethyl)-phosphonium (THP) salt or a tetrakis-(hydroxymethyl)-phosphonium hydroxide (THPOH) salt, wherein the anion A$^-$ is selected from the group consisting of formate, acetate, phosphate, sulphate, fluoride, chloride, bromide and iodide.

In a salt of a compound of any one of formula (XII) to (XIV), the anion may be an anion selected from halogenides such as chloride, bromide and iodide, hexafluorophosphate, tetrafluoroborate, tetraphenylborate, hexafluoroantimonate and trifluoromethylsulfonate.

Furthermore, the photoinitiator system may additionally comprise an aromatic tertiary phosphine compound, wherein it is preferred that the aromatic tertiary phosphine compound has the following formula (XV):

$$Z_4\text{—}R^{21} \quad (5)$$

wherein
$Z_4$ is a group of the following formula (6)

$$R^{22}(Ar)P\text{—} \quad (6)$$

wherein
$R^{22}$ represents a substituted or unsubstituted hydrocarbyl group;
Ar represents a substituted or unsubstituted aryl or heteroaryl group;
$R^{21}$ is a substituted or unsubstituted hydrocarbyl group or a group $L_3Z_4{'}$, wherein
$L_3$ is a substituted or unsubstituted divalent hydrocarbyl group which may contain a linkage selected from an ether linkage, a thioether linkage, an ester linkage, an amide linkage, and a urethane linkage and
$Z_4{'}$ has the same meaning as $Z_4$, whereby $Z_4$ and $Z_4{'}$ may be the same or different;
wherein the group $R^{22}$ and Ar may be substituted by one or more groups selected from a hydroxyl group, an oxo group, a —$NR^{23}R^{24}$ group (wherein $R^{23}$ and $R^{24}$, which may be the same or different, are selected from a hydrogen atom and $C_{1-6}$ alkyl groups), a carboxyl group, and a group having a polymerizable double bond, and
$R^{21}$ and $L_3$ may be substituted by one or more groups selected from a hydroxyl group, an oxo group, a —$NR^{25}R^{26}$ group (wherein $R^{25}$ and $R^{26}$, which may be the same or different, are selected from a hydrogen atom and $C_{1-6}$ alkyl groups), a carboxyl group, and a group having a polymerizable double bond.

In the aromatic tertiary phosphine compound of the formula (XV), moieties $Z_4$, $R^{21}$, Ar, $R^{22}$ and $L_3$ may be defined as follows:

For $R^{22}$, the monovalent hydrocarbyl group may be an alkyl group, a cycloalkyl group, a cycloalkylalkyl group, an arylalkyl group or an aryl group.

Ar represents a substituted or unsubstituted aryl or heteroaryl group. An aryl group may be selected from a phenyl group, a naphtyl group, a tolyl group, a xylyl group, and a styryl group. A heteroaryl group may be a pyridyl group.

$L_3$ is a substituted or unsubstituted divalent hydrocarbyl group which may contain a linkage selected from an ether linkage, a thioether linkage, an ester linkage, an amide linkage, and a urethane linkage. For $L_3$, the divalent hydrocarbyl group may be an alkyldiyl group, a cycloalkyldiyl group, a cycloalkylalkyl-diyl group, an arylalkyl-diyl group or an aryldiyl group. In a cycloalkylalkyl-diyl, one valency may be bonded to each of the cycloalkyl moiety or the alkyl moiety, or both valencies may be bonded to either the cycloalkyl moiety or the alkyl moiety. In a arylalkyl-diyl group, each of the aryl moiety or the alkyl moiety may be monovalent respectively, or either the aryl moiety or the alkyl moiety is divalent, while the other moiety is nonvalent. In a cycloalkylalkyl-diyl, each of the cycloalkyl moiety or the alkyl moiety may be monovalent respectively, or either the cycloalkyl moiety or the alkyl moiety is divalent, while the other moiety is nonvalent.

The following definitions apply both for the monovalent and the divalent hydrocarbyl group, therefore, for the definition of the divalent hydrocarbyl group, the suffixes "diyl" and "-diyl" are bracketed.

An alkyl(diyl) group may be straight-chain or branched $C_{1-20}$ alkyl(diyl) group, typically a $C_{1-8}$ alkyl(diyl) group. Examples for a $C_{1-6}$ alkyl(diyl) group can include linear or branched alkyl(diyl) groups having 1 to 6 carbon atoms, preferably 1 to 4 carbon atoms, for example, methyl(diyl), ethyl(diyl), n-propyl(diyl), isopropyl(diyl), n-butyl(diyl), isobutyl(diyl), sec-butyl(diyl), tert-butyl(diyl), n-pentyl (diyl), isopentyl(diyl) and n-hexyl(diyl).

A cycloalkyl(diyl) group may be a $C_{3-20}$ cycloalkyl(diyl) group. Examples of the cycloalkyl(diyl) group can include those having 3 to 14 carbon atoms, for example, cyclopropyl (diyl), cyclobutyl(diyl), cyclopentyl(diyl) and cyclohexyl (diyl). A cycloalkylalkyl(diyl) group can include those having 4 to 20 carbon atoms.

A cycloalkylalkyl(-diyl) group can include a combination of a linear or branched alkyl(diyl) group having 1 to 6 carbon atoms and a cycloalkyl(diyl) group having 3 to 14 carbon atoms. Examples of the cycloalkylalkyl(-diyl) group can for example, include methylcyclopropyl(-diyl) methylcyclobutyl(-diyl), methylcyclopentyl(-diyl), methylcyclohexyl(-diyl), ethylcyclopropyl(-diyl), ethylcyclobutyl(-diyl), ethylcyclopentyl(-diyl), ethylcyclohexyl(-diyl), propylcyclopropyl(-diyl), propylcyclobutyl(-diyl), propylcyclopentyl(-diyl), propylcyclohexyl(-diyl).

An arylalkyl(-diyl) group may be a $C_{7-20}$ arylalkyl(-diyl) group, typically a combination of a linear or branched alkyl(diyl) group having 1 to 6 carbon atoms and an aryl(-diyl) group having 6 to 10 carbon atoms. Specific examples of an arylalkyl(-diyl) group are a benzyl(-diyl) group or a phenylethyl(-diyl) group.

An aryl(diyl) group can include aryl(diyl) groups having 6 to 10 carbon atoms. Examples of the aryl(diyl) group are phenyl(diyl) and naphtyl(diyl). Aryl(diyl) groups may contain 1 to 3 substituents. Examples of such substituents can include halogen atoms, a cyano group, a hydroxy group, an amino group, $C_{1-6}$ alkyl groups and $C_{1-6}$ alkoxy groups. Here, illustrative of the halogen atoms can be fluorine, chlorine, bromine and iodine. The $C_{1-4}$ alkyl(diyl) groups are, for example, methyl(diyl), ethyl(diyl), n-propyl(diyl), isopropyl(diyl) and n-butyl(diyl). Illustrative of the $C_{1-4}$ alkoxy(diyl) groups are, for example, methoxy(diyl), ethoxy (diyl) and propoxy(diyl). The alkyl(diyl) moieties in these substituents may be linear, branched or cyclic.

Preferably, the hydrocarbyl group is an aryl(diyl) group selected from a phenyl(diyl) group and a naphthyl(diyl) group, which groups may optionally be substituted by one to three groups selected from halogen atoms, a cyano group, an amino group, a hydroxy group, $C_{1-6}$ alkyl groups and $C_{1-6}$ alkoxy groups, or wherein the hydrocarbyl group is a non-aromatic hydrocarbyl group selected from a straight chain or branched alkyl group, a straight chain or branched alkenyl group, or a straight chain or branched alkynyl group.

The $C_{1-8}$ alkyl(diyl) group and the $C_{3-14}$ cycloalkyl(diyl) group may optionally be substituted by one or more members of the group selected from a $C_{1-4}$ alkyl group, $C_{1-4}$ alkoxy group, a phenyl group, and a hydroxy group. Examples for a $C_{1-4}$ alkyl group can include linear or branched alkyl groups having 1 to 4 carbon atoms, for example, methyl, ethyl, n-propyl, isopropyl, n-butyl, isobutyl, sec-butyl, tert-butyl. Examples for an $C_{1-4}$ alkoxy group can include linear or branched alkoxy groups having 1 to 4 carbon atoms, for example, methoxy, ethoxy, n-propoxy, isopropoxy, n-butoxy, isobutoxy, sec-butoxy, and tert-butoxy.

Moreover, in formula (XV), any of the hydrocarbyl group may be substituted by one or more groups selected from halogen atoms, a cyano group, an amino group or a hydroxy group.

Accordingly, in the hydrocarbyl groups some or all hydrogen atoms are replaced by halogen atoms (e.g., fluoro, bromo, chloro), for example, halo-substituted alkyl groups such as chloromethyl, chloropropyl, bromoethyl and trifluoropropyl, and cyanoethyl.

In case the hydrocarbyl group contains an alkyl(diyl) chain, one or more carbon atoms in the alkyl(diyl) chain may be replaced by an oxygen atom, a sulfur atom, an amide group, an ester group, or a urethane group. In case the hydrocarbyl group is an alkyl group having more than one carbon atom, the alkyl group contains an alkylene. Accordingly, in case the hydrocarbyl group is an n-hexyl group, any of the carbon atoms of the alkylene chain excluding the terminal methyl group may be replaced by an oxygen atom, a sulfur atom, an amide group, an ester group, a urethane group or an NH group. Therefore, the following groups may be given as specific examples in case of one or more oxygen atoms:

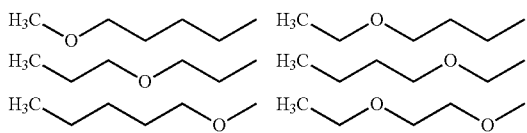

In formula (XV), group $R^{22}$ and/or Ar as well as $R^{21}$ and/or $L_3$ may be substituted with a polymerizable double bond, preferably a carbon-carbon double bond. Examples of polymerizable carbon-carbon double bonds include vinyl, conjugated vinyl, allyl, acryl, methacryl and styryl. Preferably, the polymerizable double bond is selected from the group consisting of methacryl, acryl and styryl. More preferably, the double bond is styryl.

Preferably, $R^{26}$ and Ar independently are aromatic hydrocarbyl groups selected from a phenyl group, a naphtyl group, a tolyl group, a xylyl group, and a styryl group.

As regards $R^{21}$, this moiety is preferably an aryl group, which may be substituted by one or more groups selected from a hydroxyl group, an amino group, a —$NR^{25}R^{26}$ group (wherein $R^{25}$ and $R^{26}$, which may be the same or different, are selected from $C_{1-6}$ alkyl groups), a carboxyl group, and a group having a polymerizable double bond. Alternatively, $R^{21}$ is preferably a group $L_3Z_4'$ wherein $Z_4'$ and $Z_4$ are the same.

More preferably, $R^{21}$ is a $C_{1-6}$ alkyl group or a $C_{1-6}$ alkenyl group, which groups may be substituted by one or more groups selected from a hydroxyl group, an amino group, a —$NR^{25}R^{26}$ group (wherein $R^{25}$ and $R^{26}$, which may be the same or different, are selected from $C_{1-6}$ alkyl groups), a carboxyl group, and a group having a polymerizable double bond. The group having a polymerizable double bond may be vinyl group, an allyl group, a (meth) acryloyloxy group or a (meth) acryloylamido group.

Even more preferably, the aromatic phosphine compound is a compound of formula (XV) wherein $Z_4$ is a group of the following formula:

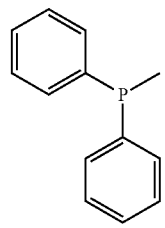

Specific examples for a compound of formula (XV) include triphenyl phosphine (TPP), 4-(diphenylphosphino) styrene (DPPS), 4-(diphenylphosphino)benzoic acid, 4-(diphenylphosphino) benzoic acid, 3-(diphenylphophonino) propionic acid, (4-(diphenylphosphino) N,N'-dimethylaniline, 2,2'-bis(diphenylphosphino)benzophenone (BDPPEP), bis[2-(diphenylphosphino)phenyl]ether (BDPPE), (4-Hydroxyphenyl)diphenylphosphine, allyldiphenylphosphine. Preferably, the compound of formula (XV) is triphenyl phosphine (TPP) or 4-(diphenylphosphino)styrene (DPPS), more preferably 4-(diphenylphosphino)styrene (DPPS).

According to (e), the aqueous dental composition comprises a stabilizer. The aqueous dental composition may comprise one or more stabilizer(s) of the formula (VII) and/or (VIII).

The term "stabilizer" as used herein means any compound capable of preventing polymerizable compounds contained in the aqueous dental composition from spontaneous polymerization during storage. However, the stabilizer does not disturb or prevent intended polymerisation curing of the aqueous dental composition during application.

Preferably, the stabilizer is a compound of the following formula (VII) and/or (VIII):

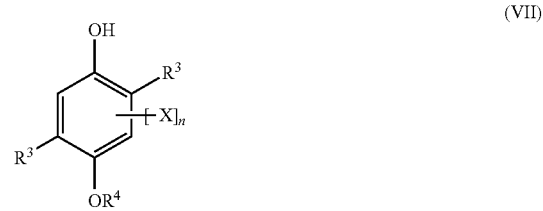

(VII)

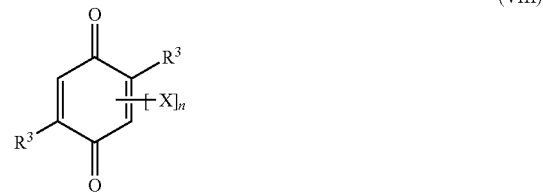

(VIII)

wherein
the $R^3$, which may be the same or different, independently represent a branched $C_{3-8}$ alkyl group or alkenyl or a $C_{3-8}$ cycloalkyl or cycloalkenyl group,
$R^4$ represents a hydrogen atom, $C_{1-6}$ alkyl or $C_{2-6}$ alkenyl group, or a $C_{1-6}$ fluoroalkyl or $C_{2-6}$ fluoroalkenyl group,
X represents a group selected from a $C_{1-8}$ alkyl group or a $C_{3-8}$ cycloalkyl group, and
n is 0, 1 or 2.

It was surprisingly found that the class of stabilizers of formula (VII) and/or (VIII) provides for full or at least substantial avoidance of discoloration upon storage and/or during photocuring. In particular, this class of stabilizers provides for a surprising stabilizing effect in an acidic aqueous mixture so that an aqueous dental composition having a pH of at most 7 may be provided which has no or substantially no discoloration upon storage and an excellent storage stability due to an improved resistance against premature polymerization.

More preferably, the stabilizer is a compound of formula (VII) and/or (VIII) wherein the $R^3$, which may be the same or different, independently represent a branched $C_{3-8}$ alkyl group or a $C_{3-8}$ cycloalkyl group, and $R^4$ represents hydrogen atom, a $C_{1-6}$ alkyl group or a $C_{1-6}$ fluoroalkyl group, and n is 0 or 1. Even more preferably, the stabilizer is a compound of formula (VII) and/or (VIII) wherein the $R^3$, which may be the same or different, independently represent a branched $C_{3-8}$ alkyl group and $R^4$ represents hydrogen atom or a $C_{1-6}$ alkyl group, and n is 0. Most preferably, the stabilizer is a compound of the following formulae (VIIa), (VIIb) or (VIIa):

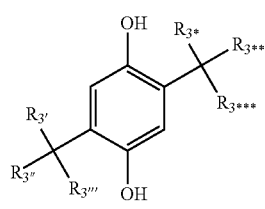
(VIIa)

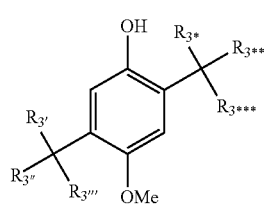
(VIIb)

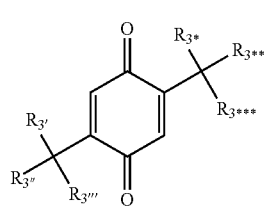
(VIIIa)

wherein $R_{3'}$, $R_{3''}$, $R_{3'''}$, $R_{3*}$, $R_{3}$ and $R_{3*}$, which may be the same or different, independently represent a methyl or an ethyl group. It is particularly preferred that the stabilizer of formulae (VIIa), (VIIb) or (VIIIa) is a compound of the following formulae:

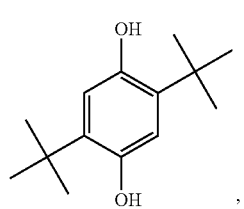
(DTBHQ)

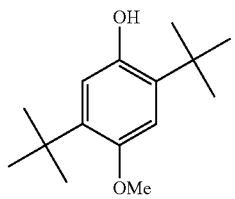
(DTBMP)

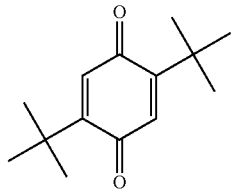
(DTBBQ)

preferably DTBHQ.

2,5-di-tert-butyl-hydroquinone (DTBHQ), 2,5-di-tert-butyl-4-methoxyphenol and 2,5-di-tert-butyl-benzoquinone (DTBBQ) are commercially available standard chemicals. In general, monoether compounds of formula (VII) such as 2,5-di-tert-butyl-hydroquinone monoalkylethers of formula (VIb) may be readily obtained from a dihydroquinone of formula (VII), such as DTBHQ, as starting material by means of selective monoetherification catalyzed in the presence of $NaNO_2$ in combination with an inorganic acid such $H_2SO_4$ or a solid acidic catalyst such as a styrene based sulfonated polymer, e.g. the commercially available ion exchange resins Amberlyst® 15 and Aberlite® IR120, analogously as described by C. Gambarotti et al. in Current Organic Chemistry 2013, 17, pages 1108 to 1113. Alternatively, monoether compounds of formula (VII) such as 2,5-di-tert-butyl-hydroquinone monoalkylethers of formula (VIb) may be obtained by reacting a dihydroquinone of formula (VII), such as DTBHQ, with an alkyl alcohol in the presence of a transition metal salt selected from copper and iron salts analogously as described in the U.S. Pat. No. 4,469,897.

The stabilizer DTBHQ is particularly preferred, since from the present experimental Example it appears that this stabilizer provides the best results in view of the discoloration problematic, i.e. there is no or almost no discoloration of the aqueous dental composition upon storage at 50° C. for 30 days, or at 60° C. or 70° C. for at least 3 days.

Discoloration upon storage and/or during photocuring may be determined according to ISO 7491:2000(en).

The aqueous dental composition according to the invention contains the stabilizer in an amount of 0.001 to 1 percent by weight, preferably 0.005 to 0.8 percent by weight based on the total weight of the composition. When the amount of the stabilizer (iii) is below the above indicated lower limit of 0.001, then storage stability of the aqueous dental composition might be insufficient, since the amount of stabilizer is too small to provide a stabilizing effect. However, when the amount of stabilizer (iii) is above the maximum threshold of 1 percent by weight, then the applicability of the aqueous dental composition might be negatively affected, since higher amounts of stabilizer may disturb or even substantially prevent intended polymerisation curing of the aqueous dental composition during application.

According to (f), the aqueous dental composition of the present invention comprises a solvent mixture comprising water and an organic solvent. The solvent mixture may comprise one or more organic solvent(s).

The term "organic solvent" as used herein means any organic compound which is fluid or liquid at room temperature and which is capable of dissolving or at least partly dissolving the components according to (a), (b), (c), (d) and (e) of the present aqueous dental composition. The organic solvent is suitably selected in view of its volatility and physiological harmlessness. Preferably, the organic solvent is more volatile than water, that is it has a vapour pressure higher than water at 20° C. Besides, it is preferred that the organic solvent is non-toxic for the patient to be treated, in particular for a human patient.

Preferably, the organic solvent of the solvent mixture is selected from the group consisting of n-propanol, iso-propanol, n-butanol, iso-butanol, sec-butanol, tert-butanol, acetone and methyl ethyl ketone. Preferably, the aqueous dental composition comprises the solvent mixture in an amount of 25 to 50 percent by weight, more preferably 27 to 47 percent by weight, most preferably 29 to 44 percent by weight based on the total weight of the aqueous dental composition.

It is preferred that according to (f), the organic solvent comprised in the solvent mixture is n-propanol or iso-propanol, preferably iso-propanol.

Preferably, the solvent mixture according to (f) comprises water in an amount of at least 1 percent by weight, more preferably at least 8 percent by weight, most preferably at least 16 percent by weight based on the total weight of the composition.

It is preferred that the sum of the masses of the above described components (a) to (f) amounts to 100% by weight based on the total weight of the composition. However, this sum may also amount to less than 100%, preferably 90%, more preferably 80%, most preferably 70% by weight based on the total weight of the composition.

The remaining part of the aqueous dental composition having a pH of at most 7 which sum of components (a) to (f) amounts to less than 100% by weight based on the total weight of the composition may be constituted by further components. Such further components may be, for example, a polymerizable monomer having at least three polymerizable double bonds, a polymerizable monomer having one or two polymerizable double bonds and a particulate filler, which are described in the following.

The aqueous dental composition according to the invention may further comprise one or more polymerizable monomer(s) having at least three polymerizable double bonds.

Preferably, the polymerizable monomer having at least three polymerizable double bonds is selected from the group consisting of trimethylolethane triacrylate, trimethylolethane trimethacrylate, trimethylolpropane triacrylate, trimethylolpropane trimethacrylate, and tri- and tetra-acrylates and methacrylates of pentaerythritol and dipentaerythritol.

Besides, the aqueous dental composition according to the present invention may further comprise one or more polymerizable monomers preferably having one or two polymerizable double bond(s).

Preferably, the one or more polymerizable monomer(s) having one or two polymerizable double bond(s) is/are selected from the group consisting of (meth)acrylate compound(s), N-substituted or N-unsubstituted alkyl acrylic or acrylic acid amide compound(s), mono-, bis- or poly(meth)acrylamides and bis(meth)acrylamide compounds. More preferably, the one or more polymerizable monomers having a polymerizable double bond includes a (meth)acrylamide, a (meth)acrylic acid ester and/or a bis(meth)acrylamide compound.

The (meth)acrylate compound may be selected from the group of methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate (HEMA), hydroxypropyl acrylate, hydroxypropyl methacrylate, tetrahydrofurfuryl acrylate, tetrahydrofurfuryl methacrylate, glycidyl acrylate, glycidyl methacrylate, the diglycidyl methacrylate of bis-phenol A ("bis-GMA"), glycerol mono- and di-acrylate, glycerol mono- and dimethacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate (where the number of repeating ethylene oxide units vary from 2 to 30 especially triethylene glycol dimethacrylate (TEGDMA), neopentyl glycol diacrylate, neopentylglycol dimethacrylate, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate, di-2-methacryloyloxyethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethyl-hexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methy-2-methacryloxyethyl-dimethylbenzene dicarbamate, di-1-methyl-2-metha-cryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl4-cyclohexyl carbamate, 2,2'-bis(4-methacryloxyphenyl)propane, 2,2'bis(4-acryloxyphenyl) propane, 2,2'-bis[4(2-hydroxy-3-methacryloxy-phenyl)] propane, 2,2'-bis[4(2-hydroxy-3-acryloxy-phenyl)propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl) propane, 2,2'-bis(4-acryloxydiethoxyphenyl)propane, 2,2'-bis[3(4-phenoxy)-2-hydroxypropane-1-methacrylate] propane, and 2,2'-bis[3(4-phenoxy)-2-hydroxypropane-1-acryalte]propane, may be mentioned.

The N-substituted alkyl acrylic or acrylic acid amide compound(s) are preferably characterized by one of the following formulas:

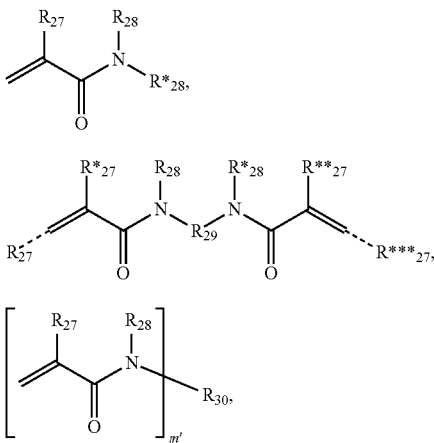

wherein $R_{27}$, $R^*_{27}$, $R^{}_{27}$, $R^{*}_{27}$ independently represent a hydrogen atom, —COOM, a straight chain or branched $C_1$ to $C_{18}$ alkyl group which may be substituted by a $C_{3-6}$ cycloalkyl group, a $C_{6-14}$ aryl or $C_{3-14}$ heteroaryl group, —COOM, —PO$_3$M, —O—PO$_3$M$_2$ or —SO$_3$M, a $C_3$ to $C_{18}$ cycloalkyl group which may be substituted by a $C_{1-6}$ alkyl group, a $C_{6-14}$ aryl or $C_{3-14}$ heteroaryl group, —COOM, —PO$_3$M, —O—PO$_3$M$_2$ or —SO$_3$M, or a $C_5$ to $C_{18}$ aryl or $C_3$ to $C_{18}$ heteroaryl group which may be substituted by —COOM, —PO$_3$M, —O—PO$_3$M$_2$ or —SO$_3$M, $R_{28}$ and $R^*_2$ independently represent a hydrogen atom, a straight chain or branched $C_1$ to $C_{13}$ alkyl group or $C_2$ to $C_{18}$ alkenyl group which may be substituted by a $C_{3-6}$ cycloalkyl group, a $C_{6-14}$ aryl or $C_{3-14}$ heteroaryl group, —COOM, —PO$_3$M, —O—PO$_3$M$_2$ or —SO$_3$M, a $C_3$ to $C_{18}$ cycloalkyl group which may be substituted by a $C_{1-16}$ alkyl group, a $C_{6-14}$ aryl or $C_{3-14}$ heteroaryl group, —COOM, —PO$_3$M, —O—PO$_3$M$_2$ or —SO$_3$M, or a $C_5$ to $C_{18}$ aryl or $C_3$ to $C_{18}$ heteroaryl group which may be substituted by —COOM, —PO$_3$M, —O—PO$_3$M$_2$ or —SO$_3$M, $R_{29}$ represents a divalent substituted or unsubstituted organic residue having from 13 to 45 carbon atoms, whereby said organic residue may contain from 1 to 14 carbonyl groups or heteroatoms selected from oxygen, nitrogen and sulphur; preferably $R_{29}$ is a $C_{13}$ to $C_{28}$ alkylene group or a $C_{13}$ to $C_{28}$ alkenylene group, which may contain 1 to 6 carbonyl groups or heteroatoms selected from oxygen, nitrogen and sulfur, and which may be substituted by a hydroxyl group, a $C_{6-14}$ aryl group, —COOM, —PO$_3$M, —O—PO$_3$M$_2$ or —SO$_3$M, wherein in said $C_{13}$ to $C_{28}$ alkylene group and said $C_{13}$ to $C_{28}$ alkenylene group, from 1 to 6 —CH$_2$-groups may be replaced by a —N—(C=O)—CR$_{31}$=CH$_2$ group wherein $R_{31}$ is a hydrogen atom or a $C_1$ to $C_{18}$ alkyl group, a substituted or unsubstituted $C_3$ to $C_{18}$ cycloalkyl group, a substituted or unsubstituted $C_4$ to $C_{18}$ aryl or heteroaryl group, a substituted or unsubstituted $C_5$ to $C_{18}$ alkylaryl or alkylheteroaryl group, a substituted or unsubstituted $C_7$ to $C_{30}$ aralkyl group, and a substituted or unsubstituted $C_2$ to $C_{45}$ mono-, di- or polyether group having from 1 to 14 oxygen atoms, $R_{30}$ represents a saturated di- or multivalent substituted or unsubstituted $C_2$ to $C_{18}$ hydrocarbon group, a saturated di- or multivalent substituted or unsubstituted cyclic $C_3$ to $C_{18}$ hydrocarbon group, a di- or multivalent substituted or unsubstituted $C_4$ to $C_{18}$ aryl or heteroaryl group, a di- or multivalent substituted or unsubstituted $C_5$ to $C_1$ alkylaryl or alkylheteroaryl group, a di- or multivalent substituted or unsubstituted $C_7$ to $C_{30}$ aralkyl group, or a di- or multivalent substituted or unsubstituted $C_2$ to $C_{45}$ mono-, di-, or polyether residue having from 1 to 14 oxygen atoms, and m is an integer, preferably in the range from 1 to 10, wherein M of any one $R_{27}$, $R^*_{27}$, $R^{}_{27}$, $R^{*}_{27}$, $R_{28}$, $R^*_{28}$, $R_{29}$ and $R_{30}$, which M are independent from each other, each represent a hydrogen atom or a metal atom.

For $R_{28}$, $R^*_{28}$ and $R_{29}$, the term "$C_3$ to $C_{18}$ cycloalkyl group" includes polycycloalkyl groups comprising two or more cycloalkyl groups, wherein at least two rings share one C—C bond. Preferred are $C_5$ to $C_{14}$ polycycloalkyl groups, more preferred are $C_8$ to $C_{12}$ polycycloalkyl groups, and most preferred are tricyclo[5.2.1.0$^{2,6}$]decyl or adamantyl.

In compound of formula (A), $R_{28}$ and $R^*_{28}$ may cooperatively form a ring in which $R_{28}$ and $R_{28}*$ are linked by a C—C bond or a functional group selected from the group consisting of an ether group, a thioether group, an amine group and an amide group.

Mono-, bis- or poly(meth) acrylamide preferably have the following formulae:

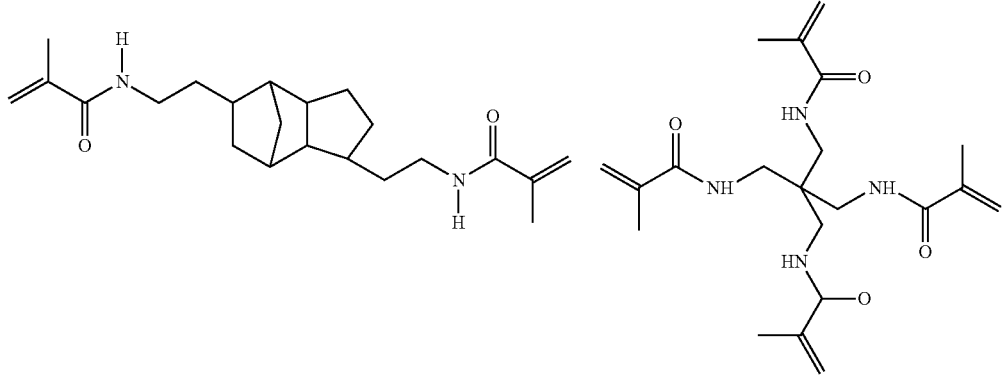

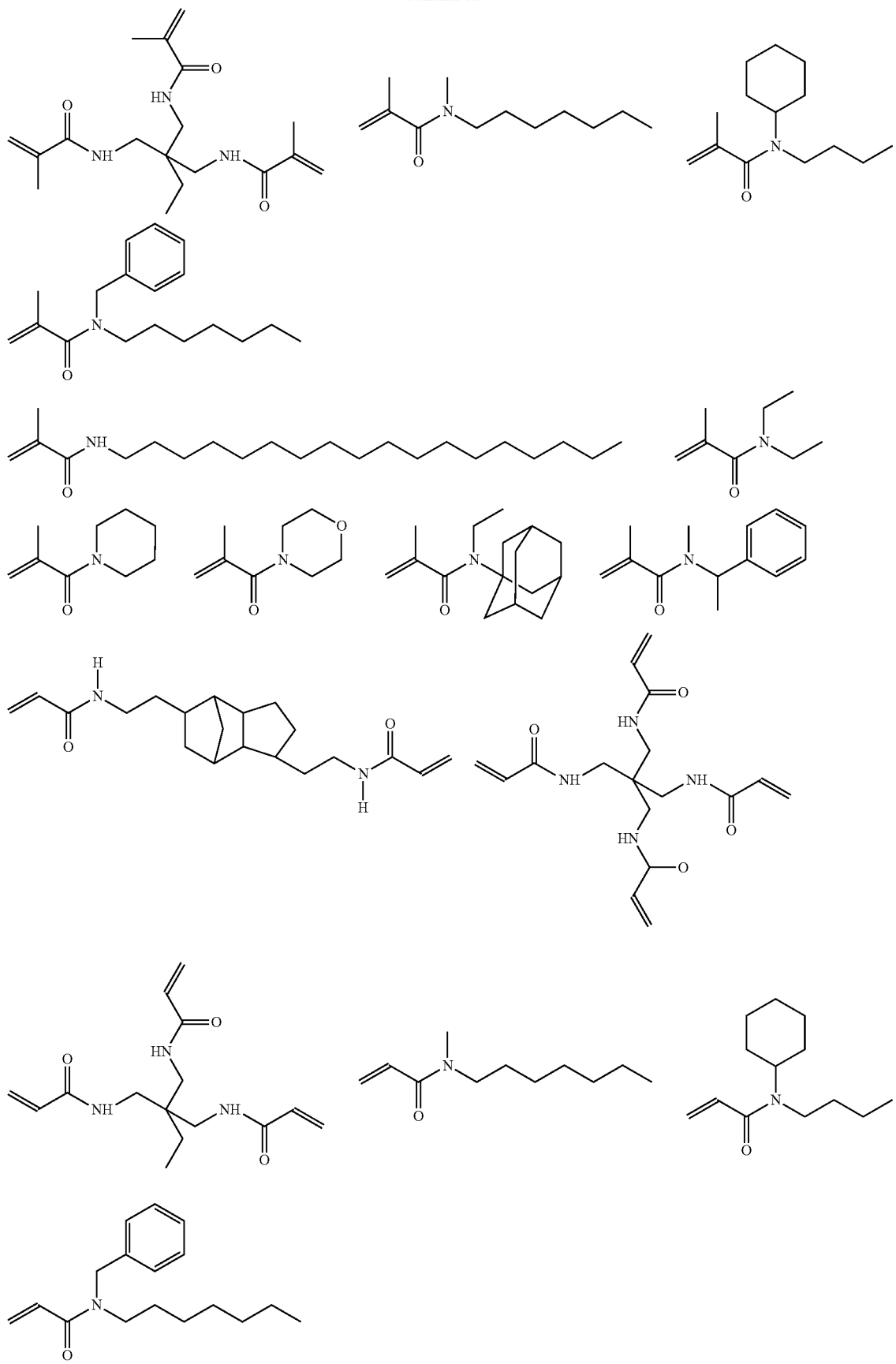

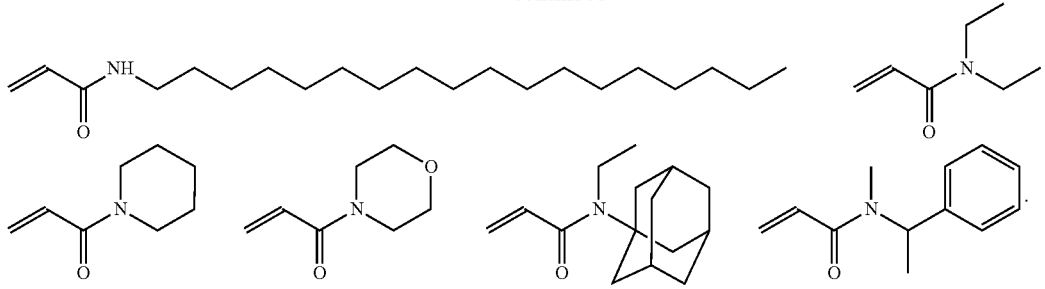

Other suitable examples of polymerizable monomers having a polymerizable double bond are isopropenyl oxazoline, vinyl azalactone, vinyl pyrrolidone, styrene, divinylbenzene, urethane acrylates or methacrylates, epoxy acrylates or methacrylates and polyol acrylates or methacrylates.

It is preferred to select the above described polymerizable monomers with the proviso that they do not contain ester groups, or at least only ester groups which do not hydrolyze in aqueous media at pH 3 at room temperature within one month. Thereby, an advantageous stability of the aqueous dental composition having a pH of at most 7 in terms of shelf-life stability of the uncured dental composition as well as stability after curing in the mouth of a patient is ensured.

Preferably, the aqueous dental composition according to the present invention further comprises a particulate filler. The aqueous dental composition may comprise one or more particulate filler(s). The aqueous dental composition of the present invention may preferably comprise the particulate filler in an amount of 0.1 to 80 percent by weight based on the total weight of the composition.

The particulate filler may be in inorganic or organic form or a mixture of at least two components selected from inorganic and organic component. The particulate filler may in the form of a reactive or non-reactive filler.

Suitable particulate fillers may be selected from fillers currently used in dental compositions. The filler should be finely divided and preferably has a maximum particle diameter less than about 100 µm and an average particle diameter less than about 10 µm. The filler may have a unimodal or polymodal (e.g., bimodal) particle size distribution. The particle size may be measured, for example, by electron microscopy or by using a conventional laser diffraction particle sizing method as embodied by a MALVERN Mastersizer S or MALVERN Mastersizer 3000 apparatus. The particulate filler may be a multimodal particulate non-reactive filler representing a mixture of two or more particulate fractions having different average particle sizes. The particulate reactive filler may also be a mixture of particles of different chemical composition. The particulate non-reactive filler may be surface modified by a surface modifying agent.

The filler can be an inorganic material. It can also be a crosslinked organic material that is insoluble in the polymerizable resin, and is optionally filled with inorganic filler. The filler can be radiopaque. Examples of suitable particulate inorganic fillers are naturally-occurring or synthetic materials such as quartz, nitrides such as silicon nitride, glasses derived from, for example Ce, Sb, Sn, Zr, Sr, Ba and Al, colloidal silica, feldspar, borosilicate glass, kaolin, talc, titania, and zinc glass, and submicron silica particles such as pyrogenic silicas.

Examples of suitable non-reactive organic filler particles include filled or unfilled pulverized polycarbonates or polyepoxides. Preferably the surface of the filler particles is treated with a coupling agent in order to enhance the bond between the filler and the matrix. The use of suitable coupling agents include gamma-methacryloxypropyltrimethoxysilane, gamma-mercaptopropyltriethoxysilane, gamma-aminopropyltrimethoxysilane, and the like.

The particulate filler may also be a filler obtainable by a process for the preparation of composite filler particles, comprising:

1) coating a particulate filler having a median particle size (D50) of from 1 to 1200 nm with a coating composition containing a film-forming agent forming a coating layer on the surface of the particulate filler, said coating layer displaying reactive groups on the surface of the coating layer, said reactive groups being selected from addition polymerizable groups and step-growth polymerizable groups, thereby forming a coated particulate filler; subsequently or concurrently 2) agglomerating the coated particulate filler, optionally in the presence of a further crosslinking agent and optionally in the presence of a further particulate filler not displaying reactive groups, for providing a granulation of the coated particulate filler wherein the granulation contains the coated particulate filler particles and the optional further particulate filler particles separated from and connected to each other by at least one coating layer, whereby the at least one coating layer may be crosslinked by crosslinking groups obtained by reacting the reactive groups and optionally a further crosslinking agent;

3) optionally milling, classifying and/or sieving the granulation of the coated particulate filler; and 4) optionally further crosslinking the granulation of the coated particulate filler; for providing composite filler particles having a median particle size (D50) of from 1 to 70 µm, wherein reactive groups are transformed into crosslinking groups obtained by reacting reactive groups and optionally a further crosslinking agent, and wherein the particulate filler is the main component by volume of the composite filler particles as further described in EP-A 2 604 247.

Preferably, the aqueous dental composition according to the present invention comprises a reactive particulate glass as particulate filler.

The term "reactive particulate glass" means a solid mixture of metal oxides, wherein the mixture is in particulate form. Specific examples of particulate reactive fillers are selected from calcium alumino silicate glass, calcium alumino fluorosilicate glass, calcium aluminumfluoroborosilicate glass, strontium aluminosilicate glass, strontium aluminofluorosilicate glass, strontium aluminofluoroborosilicate glass. Suitable particulate reactive fillers may be in the form of metal oxides such as zinc oxide and/or magnesium oxide, and/or in the form of ion-leachable glasses, e.g., as described in U.S. Pat. Nos. 3,655,605, 3,814,717, 4,143,018, 4,209,434, 4,360,605 and 4,376,835.

Preferably, the reactive particulate glass is a reactive particulate glass comprising:
1) 20 to 45% by weight of silica,
2) 20 to 40% by weight of alumina,
3) 20 to 40% by weight of strontium oxide,
4) 1 to 10% by weight of $P_2O_5$, and
5) 3 to 25% by weight of fluoride.

Furthermore, it is preferred that the present dental composition comprises 0.1 to 80, preferably 0.5 to 60, more preferably 1 to 40 percent by weight of the reactive particulate glass, based on the weight of the entire weight of the aqueous dental composition.

The reactive particulate glass usually has an average particle size of from 0.005 to 100 μm, preferably of from 0.01 to 40 μm as measured, for example, by electron microscopy or by using a conventional laser diffraction particle sizing method as embodied by a MALVERN Mastersizer S or MALVERN Mastersizer 3000 apparatus.

The reactive particulate glass may be surface modified by a surface modifying agent.

Preferably, the surface modifying agent is a silane. A silane provides a suitable hydrophobicity to the reactive particulate glass, which allows for an advantageous, homogeneous admixture with the organic components of the present aqueous dental composition.

Furthermore, it is preferred to include non-reactive fillers in the present aqueous dental composition for changing the appearance of the composition, for controlling viscosity of the composition, for further improving mechanical strength of a dental glass ionomer cement obtained from the composition, and e.g. for imparting radiopacity. The non-reactive filler should be non-toxic and suitable for use in the mouth.

The filler may be in the form of an inorganic material. It can also be a crosslinked organic material that is insoluble in the polymerizable polymer according to (B) comprised in the present aqueous dental glass ionomer composition, and is optionally filled with inorganic filler.

For example, suitable non-reactive inorganic fillers may be quartz, nitrides such as silicon nitride, colloidal silica, submicron silica such as pyrogenic silicas, colloidal zirconia, feldspar, borosilicate glass, kaolin, talc or a metallic powder comprising one or more metals or metal alloys.

Examples of suitable non-reactive organic fillers include filled or unfilled particulate polycarbonates or polyepoxides. Preferably the surface of the non-reactive organic filler particles is treated with a coupling agent in order to enhance the bond between the filler and the matrix. Suitable coupling agents include silane compounds such as gamma-methacryloxypropyltrimethoxysilane, gamma-mercaptopropyltriethoxysilane and gamma-aminopropyltrimethoxysilane.

According to a particularly preferred embodiment, the aqueous dental composition having a pH of at most 7 comprises:
(a) 20 to 60 percent by weight based on the total weight of the composition of a polymerizable compound of the following formula (I):

A-L-B  (I)

wherein
A is a group of the following formula (III)

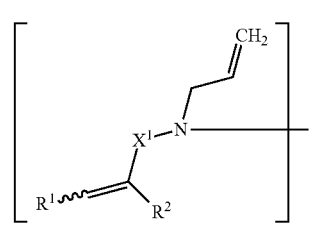

(II)

$X^1$ is CO or $CH_2$;
$R^1$ is a hydrogen atom,
$R^2$ is a hydrogen atom, a methyl group or —$CH_2$—COOM, preferably $X^1$ is CO and $R^2$ is a hydrogen atom or a methyl group, more preferably $X^1$ is CO and $R^2$ is a hydrogen atom,
L is a divalent $C_{2-12}$ alkenylene linker group, which may contain 1 to 3 carbonyl groups or nitrogen atom(s), and which may be substituted by a hydroxyl group, preferably L is an unsubstituted divalent $C_{3-8}$ alkenylene linker group, more preferably L is —$CH_2$—CH=CH—$CH_2$—;
B is a group according to the definition of A,
(b) 3 to 15 percent by weight based on the total weight of the composition of a polymerizable compound of the following formula (V):

A'-L'-A'  (V)

wherein the
A' which are independent from each other, each represent a group of the following formula (VI)

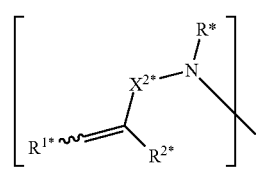

(VI)

wherein
$X^{2*}$ is CO,
$R^{1*}$ is a hydrogen atom,
$R^{2*}$ is a hydrogen atom,
R* is an ethyl group,
L' is a divalent $C_{2-12}$ alkylene linker group, which may contain 1 to 3 carbonyl groups or nitrogen atom(s), and which may be substituted by a hydroxyl group, preferably L' is an unsubstituted divalent $C_{2-8}$ alkylene linker group, more preferably L' is n-propylene;
(c) 1 to 20 percent by weight based on the total weight of the composition of a polymerizable monomer having one or more acidic groups, preferably a polymerizable phosphoric acid ester of formula (IX);
(d) 0.001 to 5 percent by weight based on the total weight of the composition of a photoinitiator system; preferably, the photoinitiator system comprises a 1,2-diketone photoinitiator compound having a light absorption maximum in the range from 300 to 500 nm
(e) 0.001 to 1 percent by weight based on the total weight of the composition of a stabilizer of formula (VII) and/or (VIII); and (f) 25 to 50 percent by weight based on the total weight of the composition of a solvent mixture comprising water and an organic solvent selected the group consisting of ethanol, n-propanol, iso-propanol, n-butanol, iso-butanol, sec-butanol, tert-butanol, acetone and methyl ethyl ketone; preferably the organic solvent is n-propanol or iso-propanol, more preferably iso-propanol.

A composition comprising at least a) a polymerizable compound of the formula (I) and b) a polymerizable compound of the formula (V) may be used for the preparation of an aqueous dental composition, preferably an aqueous dental composition having a pH of at most 7.

For this use, the compounds of formulae (I) and (V) as defined above for the aqueous dental composition having a pH of at most 7 according to claim 1 may be used alone or in combination with any components suitable for the preparation of a dental composition. Preferably, compounds of formulae (I) and (V) are used alone or in combination with at least one of components c), d), e) and f) defined for the aqueous composition having a pH of at most 7 and optionally with further components described above for the aqueous composition having a pH of at most 7.

The invention will now be further illustrated with reference to the following examples.

EXAMPLES

Introductory Remarks Concerning Wetting Characteristics and Viscosity

Wetting is a complex, time dependent process strongly affected by the surface roughness and the nature of material surface. In a first approximation, the behavior of a liquid (L) on a solid surface (S) may be described by the following parameters: surface free energy of the solid $\sigma_S$ (SFE), surface tension of the liquid $\sigma_L$ (ST), tension on the liquid/solid interface $\sigma_{L/S}$ (IT) and the contact angle $\vartheta$ (CA) at the ternary liquid/solid (L/S) towards gas/vapour (V) interface. SFE, ST and IT are area-related energy values [mN*m$^{-1}$]. CA can be positive only with values between 0° and 180°.

As a simple analysis, the static sessile drop method may be used. Accordingly, the ternary L/S/V interface is observed after an equilibrium time t at its equilibrium state forming the static contact angle $\vartheta s$. The relationship of the parameters is given by YOUNG's equation:

$$\cos \vartheta_S = (\sigma_S - \sigma_{L/S}) * \sigma_L^{-1}$$

The capability of the present aqueous dental composition to efficiently wet a tooth surface may be expressed by the static $\vartheta_S$ (sCA). For measurement of the sCA, the three phases of the ternary system L, S and V are as follows: S is a planar or structured tooth surface or any solid surface having a SFE similar to that of a tooth surface, L is the present aqueous dental composition having a pH of at most 7, and V is ambient air. On structured solid surfaces S such as enamel and dentin, a suitable scaling factor of the sCA may be introduced.

The static sessile drop measurement was carried out with a OCA-15E goniometer from DataPhysics Instruments, Filderstadt, Germany, wherein SCA20 software from DataPhysics Instruments was used for measurement analysis.

According to the present invention, for an advantageous surface wettability, the sCA $\vartheta s$ is preferably less than 25°, more preferably less than 10°, most preferably less than 5°.

The ST of the liquid, aqueous dental composition $\sigma_L$ allows for a preliminary assessment whether or not the liquid aqueous dental composition might provide for a suitable wetting of the structured tooth surface. This is because the SFE in the form of the tooth surface $\sigma s$ remains unchanged at a defined humidity level. As can be gathered from the YOUNG'S equation, while lowering $\sigma s$ provides for a higher value for cos $\sigma s$, the degree value for sCA becomes lower. Hence, once a suitable wetting providing an at least sufficiently low sCA is obtained, measurement of $\sigma_L$ provides for an uncomplicated pretesting whether or not the present aqueous dental composition may provide suitable surface wetting characteristics.

For quantification of the wettability, the contact angle $\vartheta s$ may be measured, preferably by the static sessile drop method described above.

ST $\sigma_L$ may be determined by means of any prior art determination method. For example, the value of $\sigma_L$ may be determined by WASHBURN Capillary Rise method, WILHELMY Plate or DU NOÜY Ring method, Maximum Bubble Pressure method, Pendant or Sessile Drop method, Drop Weight or Volume method and Spinning Drop method. The aforementioned methods are e.g. described in J. G. WEBSTER, "Mechanical Variables Measurement—Solid, Fluid, and Thermal", CRC Press Inc., 1999, p. 12-1 to 12-13.

In the present invention, ST $\sigma_L$ was determined by the Pendant Drop method using an OCA-15E goniometer from DataPhysics Instruments, Filderstadt, Germany, wherein SCA20 software from DataPhysics Instruments was used for measurement analysis.

According to the present invention, the surface tension ST of the liquid, aqueous dental composition $\sigma_L$ is preferably within a range of from 5 to 75 mN*m$^{-1}$, more preferably 10 to 50 mN*m$^{-1}$, and in particular 10 to 40 mN*m$^{-1}$.

Furthermore, an important parameter interrelating with sCA $\vartheta s$ and ST $\sigma_L$ is the penetration coefficient ($k_P$), which is defined as follows:

$$k_P = \sigma_L * \cos \vartheta_S * (2\eta)^{-1}$$

wherein $\eta$ is the viscosity of the aqueous dental composition.

The penetration coefficient $k_P$ is a measure of the ability of a liquid such as the aqueous dental composition to penetrate into a capillary space such as pores or cavities of the tooth surface or gingival pockets. From the above equation for $k_P$, it is understood that the higher the viscosity $\eta$, the lower $k_P$ becomes. Hence, not only in view of workability and handling comfort of the aqueous dental composition, but also in view of suitable penetration of the tooth surface, it is important to suitably set the viscosity $\vartheta s$ of the aqueous dental composition.

The viscosity was determined using a Kinexus pro+ rotation type rheometer from Malvern Instruments Ltd, Worcestershire, UK.

According to the present invention, the viscosity of the aqueous dental composition r is preferably set within a range of from 1 to 100 mPa*s more preferably 5 to 75 mPa*s, and in particular 10 to 50 mPa*s.

Preparation of Aqueous Dental Compositions

Eight different aqueous dental compositions 1 to 8 representing aqueous dental compositions according to the invention have been prepared by admixing the components listed in Table 1.

TABLE 1

Aqueous dental compositions 1 to 8

| Aqueous dental composition: | 1 | 2 | 3 | 4 | 5 | 6 | 7 | 8 |
|---|---|---|---|---|---|---|---|---|
| PENTA [wt.-%] | 0.0 | 6.5 | 6.5 | 4.4 | 6.5 | 0.5 | 5.0 | 5.0 |
| BAABE [wt.-%] | 44.4 | 47.4 | 7.3 | 41.9 | 20.0 | 45.4 | 46.4 | 46.4 |
| BADEP [wt.-%] | 3.9 | 5.4 | 20.0 | 3.5 | 7.3 | 7.5 | 4.4 | 4.4 |
| MDP [wt.-%] | 11.0 | 0.0 | 13.0 | 9.5 | 13.0 | 0.5 | 9.5 | 9.5 |
| Propan-2-ol [wt.-%] | 16.5 | 16.5 | 20.0 | 16.5 | 20.0 | 19.0 | 5.0 | 26.5 |
| Water [wt.-%] | 21.0 | 21.0 | 30.0 | 21.0 | 30.0 | 23.9 | 26.5 | 5.0 |
| CQ [wt.-%] | 1.8 | 1.8 | 1.8 | 1.8 | 1.8 | 1.8 | 1.8 | 1.8 |
| DMABN [wt.-%] | 0.6 | 0.6 | 0.6 | 0.6 | 0.6 | 0.6 | 0.6 | 0.6 |
| BMIHP [wt.-%] | 0.7 | 0.7 | 0.7 | 0.7 | 0.7 | 0.7 | 0.7 | 0.7 |
| DTBHQ [wt.-%] | 0.1 | 0.1 | 0.1 | 0.1 | 0.1 | 0.1 | 0.1 | 0.1 |
| Sum [wt.-%] | 100.0 | 100.0 | 100.0 | 100.0 | 100.0 | 100.0 | 100.0 | 100.0 |

List of abbreviations used in Table 1:
PENTA: Dipentaerythritol pentacrylate phosphate
BAABE: N,N'-(2E)-but-2-en-1,4-diallylbis-[(N-prop-2-en-1) amide
BADEP: N,N'-Diethyl-1,3-propylene bisacrylamide
MDP: 10-Methacryloyl oxydecyl dihydrogen phosphate
CQ: Camphorquinone
DMABN: Dimethylamino benzonitril
BMIHP: Bis(4-methylphenyl)iodonium hexafluorophosphate
DTBHQ: di-tert.-Butylhydroquinone Determination of pH, Viscosity, Surface Tension and Wetting Behaviour For aqueous dental compositions 1 to 8, the pH-value, viscosity, surface tension and wetting were determined. The pH was measured using a solvent-robust special electrode for partially aqueous systems. The viscosity was measured using a Kinexus pro+ rotation type rheometer from Malvern Instruments Ltd, Worcestershire, UK. The surface tension and the wetting behaviour were measured using an OCA-15E goniometer from DataPhysics Instruments, Filderstadt, Germany, wherein SCA20 software from DataPhysics Instruments was used for measurement analysis. The surface tension and the wetting behaviour were measured against ambient air under exclusion of blue light.

TABLE 2 pH-value, viscosity and surface tension obtained for aqueous dental compositions 1 to 8.

| Aqueous dental composition: | 1 | 2 | 3 | 4 | 5 | 6 | 7 | 8 |
|---|---|---|---|---|---|---|---|---|
| pH-Value | 2.7 | 2.4 | 2.2 | 2.5 | 2.1 | 3.2 | 2.3 | 3.0 |
| Viscosity [mPa*s] | 29.3 | 30.7 | 23.9 | 32.5 | 25.7 | 25.9 | 42.1 | 37.5 |
| Surface tension [mN*m$^{-1}$] | 33.7 | 32.6 | 45.9 | 33.0 | 33.2 | 32.7 | 36.5 | 30.5 |

The results listed in Table 2 show that for all aqueous dental compositions 1 to 8, the pH-value is less than 7, that is acidic. Furthermore, all aqueous dental compositions 1 to 8 have an advantageous low viscosity within the range of 10 to 50 mPa*s. The surface tension within a range of 30 to 50 mN*m$^{-1}$ is relatively low.

Furthermore, the wetting behaviour was determined on ideal moist human dentin surface prepared according to ISO 29022, and evaluated 5 sec after dosage of a droplet of the respective aqueous dental composition on the human dentin surface. For all aqueous dental compositions 1 to 8, a full wetting was obtained, that is, the contact angle after 5 sec was less than 3°.

Hence, owing to the specific combination of compounds of formula (I) and (V), such as BAABE and BADEP, the aqueous dental compositions 1 to 8 according to the invention provide for an advantageous combination of low viscosity, low surface tension and full wetting. This provides for a simplified application of the aqueous dental composition on a dental surface, while an advantageous full wetting of the dental surface is provided.

Determination of characteristics of cured aqueous dental compositions 1 to 8 The aqueous dental compositions were applied on an enamel or dentin prepared according to ISO 29022, and cured by irradiation with light. Thereafter, shear bond strength to enamel and shear bond strength to dentin was measured according to ISO 29022.

TABLE 3

Shear bond strength to enamel and dentin

| Cured Aqueous dental composition: | 1 | 2 | 3 | 4 | 5 | 6 | 7 | 8 |
|---|---|---|---|---|---|---|---|---|
| Shear bond strength enamel [MPa] | 23.0 | 19.8 | 23.4 | | 15.0 | 22.9 | | |
| Shear bond strength dentin[4] [MPa] | 35.3 | 23.7 | 32.4 | | 31.0 | 28.9 | | |

The results listed in Table 2 show that particularly advantageous shear bond strength to enamel within a value range of 15 to 25 MPa and shear bond strength to dentin within a value range of 10 to 36 MPa were obtained for the cured aqueous dental compositions 1 to 8.

The invention claimed is:

1. An aqueous dental composition having a pH of at most 7, comprising:
   (a) 1 to 70 percent by weight based on the total weight of the composition of a polymerizable compound of the following formula (I):

A-L-B  (I)

wherein
   A is a group of the following formula (II)

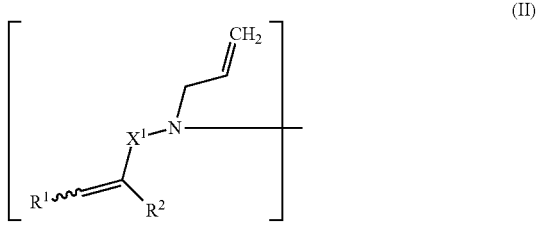

$X^1$ is CO, CS, $CH_2$, or a group $[X'Z]_k$, wherein X' is an oxygen atom, a sulfur atom or NH, Z is a straight chain or branched $C_{1-4}$ alkylene group, and k is an integer of from 1 to 10;

$R^1$ is a hydrogen atom,
—COOM,
a straight chain or branched $C_{1-16}$ alkyl group which may be substituted by a $C_{3-6}$ cycloalkyl group, a $C_{6-14}$ aryl or $C_{3-14}$ heteroaryl group, —COOM, —PO$_3$M, —O—PO$_3$M$_2$ or —SO$_3$M,
a $C_{3-6}$ cycloalkyl group which may be substituted by a $C_{1-16}$ alkyl group, a $C_{6-14}$ aryl or $C_{3-14}$ heteroaryl group, —COOM, —PO$_3$M, —O—PO$_3$M$_2$ or —SO$_3$M,
a $C_{6-14}$ aryl or $C_{3-14}$ heteroaryl group which may be substituted by —COOM, —PO$_3$M, —O—PO$_3$M$_2$ or —SO$_3$M, $R^2$ is a hydrogen atom,
—COOM
a straight chain or branched $C_{1-16}$ alkyl group which may be substituted by a $C_{6-14}$ aryl or $C_{3-14}$ heteroaryl group, —COOM, —PO$_3$M, —O—PO$_3$M$_2$ and —SO$_3$M,
a $C_{3-6}$ cycloalkyl group which may be substituted by a $C_{1-16}$ alkyl group, a $C_{6-14}$ aryl or $C_{3-14}$ heteroaryl group, —COOM, —PO$_3$M, —O—PO$_3$M$_2$ or —SO$_3$M, or
a $C_{6-14}$ aryl or $C_{3-14}$ heteroaryl group which may be substituted by —COOM, —PO$_3$M, —O—PO$_3$M$_2$ and —SO$_3$M, L is a divalent $C_{2-12}$ alkenylene linker group, which may contain 1 to 3 carbonyl groups or heteroatoms selected from oxygen, nitrogen and sulfur, and which may be substituted by a hydroxyl group, a $C_{6-14}$ aryl group, —COOM, —PO$_3$M, —O—PO$_3$M$_2$ or —SO$_3$M, wherein M is a hydrogen atom or a metal atom;

B is selected from
(i) a group according to the definition of A,
(ii) a group of the following formula (III)

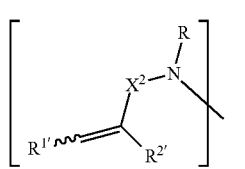

(III)

$X^2$ independently has the same meaning as defined for
$X^1$ in formula (II),
$R^{1'}$ and $R^{2'}$ are independent from each other and independently have the same meaning as defined for $R^1$ and $R^2$ in formula (II),
R is a hydrogen atom,
a straight chain or branched $C_{1-16}$ alkyl group which may be substituted by a $C_{3-6}$ cycloalkyl group, a $C_{6-14}$ aryl or $C_{3-14}$ heteroaryl group, —COOM, —PO$_3$M, —O—PO$_3$M$_2$ or —SO$_3$M,
a $C_{3-6}$ cycloalkyl group which may be substituted by a $C_{1-16}$ alkyl group, a $C_{6-14}$ aryl or $C_{3-14}$ heteroaryl group, —COOM, —PO$_3$M, —O—PO$_3$M$_2$ or —SO$_3$M,
a $C_{6-14}$ aryl or $C_{3-14}$ heteroaryl group which may be substituted by —COOM, —PO$_3$M, —O—PO$_3$M$_2$ or —SO$_3$M,
(iii) a group of the following formula (IV)

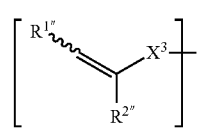

(IV)

wherein
$X^3$ is CO, —CH$_2$CO—, CS, or —CH$_2$CS—,
$R^{1''}$ and $R^{2''}$ which are independent from each other and independently have the same meaning as defined for $R^1$ and $R^2$ in formula (II), or
(iv) a group $[Z'X'']_mE$, wherein
Z' is a straight chain or branched $C_{1-4}$ alkylene group,
X'' is an oxygen atom, a sulfur atom or NH,
E is a hydrogen atom,
PO$_3$M$_2$,
a straight chain or branched $C_{1-16}$ alkyl group which may be substituted by a $C_{3-6}$ cycloalkyl group, a $C_{6-14}$ aryl or $C_{3-14}$ heteroaryl group, —COOM, —PO$_3$M, —O—PO$_3$M$_2$ or —SO$_3$M,
a $C_{3-6}$ cycloalkyl group which may be substituted by a $C_{1-16}$ alkyl group, a $C_{6-14}$ aryl or $C_{3-14}$ heteroaryl group, —COOM, —PO$_3$M, —O—PO$_3$M$_2$ or —SO$_3$M,
a $C_{6-14}$ aryl or $C_{3-14}$ heteroaryl group which may be substituted by —COOM, —PO$_3$M, —O—PO$_3$M$_2$ or —SO$_3$M, and
m is an integer of from 1 to 10; and
wherein M of any one $R^1$, $R^2$, L, R and E, which M are independent from each other, each represent a hydrogen atom or a metal atom;

(b) 2 to 20 percent by weight based on the total weight of the composition of a polymerizable compound of the following formula (V):

$$A'\text{-}L'\text{-}A' \qquad (V)$$

wherein the
A' which are independent from each other, each represent a group of the following formula (VI)

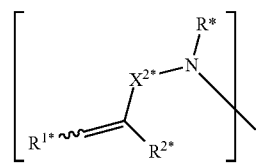

(VI)

wherein
$X^{2*}$ independently has the same meaning as defined for $X^1$ in formula (II),
$R^{1*}$ and $R^{2*}$ are independent from each other and independently have the same meaning as defined for $R^1$ and $R^2$ in formula (II),
$R^*$ is a hydrogen atom,
a straight chain or branched $C_{1-16}$ alkyl group which may be substituted by a $C_{3-6}$ cycloalkyl group, a $C_{6-14}$ aryl or $C_{3-14}$ heteroaryl group, —COOM, —$PO_3M$, —O—$PO_3M_2$ or —$SO_3M$, a $C_{3-6}$ cycloalkyl group which may be substituted by a $C_{1-16}$ alkyl group, a $C_{6-14}$ aryl or $C_{3-14}$ heteroaryl group, —COOM, —$PO_3M$, —O—$PO_3M_2$ or —$SO_3M$, a $C_{6-14}$ aryl or $C_{3-14}$ heteroaryl group which may be substituted by —COOM, —$PO_3M$, —O—$PO_3M_2$ or —$SO_3M$, L' is a divalent $C_{2-12}$ alkylene linker group, which may contain 1 to 3 carbonyl groups or heteroatoms selected from oxygen, nitrogen and sulfur, and which may be substituted by a hydroxyl group, a $C_{6-14}$ aryl group, —COOM, —$PO_3M$, —O—$PO_3M_2$ or —$SO_3M$, wherein M is a hydrogen atom or a metal atom; wherein M of any one $R^{1*}$, $R^{2*}$, L' and R*, which M are independent from each other, each represent a hydrogen atom or a metal atom;

(c) 1 to 20 percent by weight based on the total weight of the composition of one or more polymerizable monomers having one or more acidic groups;

(d) 0.001 to 5 percent by weight based on the total weight of the composition of an initiator system;

(e) 0.001 to 1 percent by weight based on the total weight of the composition of a stabilizer; and (f) 25 to 50 percent by weight based on the total weight of the composition of a solvent mixture comprising water and an organic solvent;

wherein the aqueous dental composition has storage stability for 30 days at 50° C.

2. The aqueous dental composition according to claim 1, wherein B is a group according to the definition of A.

3. The aqueous dental composition according to claim 1 or 2, wherein $X^1$ in formula (II) is CO.

4. The aqueous dental composition according to claim 1, wherein $X^2$ in formula (VI) is CO.

5. The aqueous dental composition according to claim 1, wherein L is —$CH_2CH$=$CHCH_2$—.

6. The aqueous dental composition according to claim 1, comprising a polymerizable phosphoric acid ester as a polymerizable monomer having one or more acidic groups.

7. The aqueous dental composition according to claim 1, which further comprises a polymerizable monomer having at least three polymerizable double bonds.

8. The aqueous dental composition according to claim 1, wherein the stabilizer is a compound of the following formula (VII) and/or (VIII):

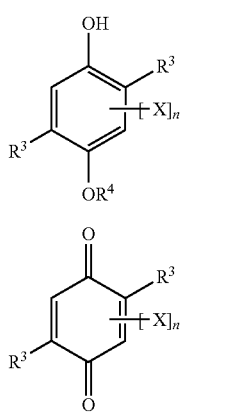

wherein the $R^3$, which may be the same or different, independently represent a branched $C_{3-8}$ alkyl or alkenyl group or a $C_{3-8}$ cycloalkyl or cycloalkenyl group, $R^4$ represents a hydrogen atom, a $C_{1-6}$ alkyl or $C_{2-6}$ alkenyl group, or a $C_{1-6}$ fluoroalkyl or $C_{2-6}$ fluoroalkenyl group, X represents a group selected from a $C_{1-8}$ alkyl group or a $C_{3-8}$ cycloalkyl group, and n is 0, 1 or 2.

9. The aqueous dental composition according to claim 1, wherein the organic solvent of the solvent mixture is selected from the group consisting of ethanol, n-propanol, iso-propanol, n-butanol, iso-butanol, sec-butanol, tert-butanol, acetone and methyl ethyl ketone.

10. The aqueous dental composition according to claim 1, wherein the solvent mixture comprises at least 1 percent by weight based on the total weight of the composition, of water.

11. The aqueous dental composition according to claim 1, which further comprises a particulate filler.

12. The aqueous dental composition according to claim 1, which is selected from a dental adhesive composition, a dental bonding agent, a dental primer, a dental infiltrant, a pit and fissure sealant, a dental desensitizing composition, a pulp capping composition, a dental composite, dental glass ionomer cement, a dental cement, a seal and protecting composition for naked tooth necks, and a dental root canal sealer composition.

13. A method of using a composition for the preparation of an aqueous dental composition having a pH of at most 7; said method comprising the step of mixing the composition comprising:

(a) 1 to 70 percent by weight based on the total weight of the composition of a polymerizable compound of the following formula (I):

A-L-B       (I)

wherein

A is a group of the following formula (II)

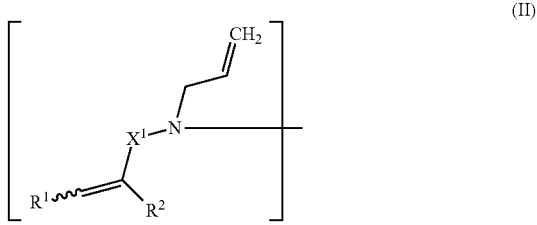

$X^1$ is CO, CS, $CH_2$, or a group $[X'Z]_k$, wherein X' is an oxygen atom, a sulfur atom or NH, Z is a straight chain or branched $C_{1-4}$ alkylene group, and k is an integer of from 1 to 10;

$R^1$ is a hydrogen atom,
—COOM,
a straight chain or branched $C_{1-16}$ alkyl group which may be substituted by a $C_{3-6}$ cycloalkyl group, a $C_{6-14}$ aryl or $C_{3-14}$ heteroaryl group, —COOM, —$PO_3M$, —O—$PO_3M_2$ or —$SO_3M$, a $C_{3-6}$ cycloalkyl group which may be substituted by a $C_{1-16}$ alkyl group, a $C_{6-14}$ aryl or $C_{3-14}$ heteroaryl group, —COOM, —$PO_3M$, —O—$PO_3M_2$ or —$SO_3M$, a $C_{6-14}$ aryl or $C_{3-14}$ heteroaryl group which may be substituted by —COOM, —$PO_3M$, —O—$PO_3M_2$ or —$SO_3M$, $R^2$ is a hydrogen atom,
—COOM
a straight chain or branched $C_{1-16}$ alkyl group which may be substituted by a $C_{6-14}$ aryl or $C_{3-14}$ heteroaryl group, —COOM, —$PO_3M$, —O—$PO_3M_2$ and —$SO_3M$,
a $C_{3-6}$ cycloalkyl group which may be substituted by a $C_{1-16}$ alkyl group, a $C_{6-14}$ aryl or $C_{3-14}$ heteroaryl group, —COOM, —$PO_3M$, —O—$PO_3M_2$ or —$SO_3M$, or
a $C_{6-14}$ aryl or $C_{3-14}$ heteroaryl group which may be substituted by —COOM, —$PO_3M$, —O—$PO_3M_2$ and —$SO_3M$, L is a divalent $C_{2-12}$ alkenylene linker group, which may contain 1 to 3 carbonyl groups or heteroatoms selected from oxygen, nitrogen and sulfur, and which may be substituted by a hydroxyl group, a $C_{6-14}$ aryl group, —COOM, —$PO_3M$, —O—$PO_3M_2$ or —$SO_3M$, wherein M is a hydrogen atom or a metal atom;

B is selected from
(i) a group according to the definition of A,
(ii) a group of the following formula (III)

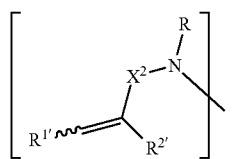
(III)

$X^2$ independently has the same meaning as defined for
$X^1$ in formula (II),
$R^{1'}$ and $R^{2'}$ are independent from each other and independently have the same meaning as defined for $R^1$ and $R^2$ in formula (II),
R is a hydrogen atom,
a straight chain or branched $C_{1-16}$ alkyl group which may be substituted by a $C_{3-6}$ cycloalkyl group, a $C_{6-14}$ aryl or $C_{3-14}$ heteroaryl group, —COOM, —$PO_3M$, —O—$PO_3M_2$ or —$SO_3M$,
a $C_{3-6}$ cycloalkyl group which may be substituted by a $C_{1-16}$ alkyl group, a $C_{6-14}$ aryl or $C_{3-14}$ heteroaryl group, —COOM, —$PO_3M$, —O—$PO_3M_2$ or —$SO_3M$,
a $C_{6-14}$ aryl or $C_{3-14}$ heteroaryl group which may be substituted by —COOM, —$PO_3M$, —O—$PO_3M_2$ or —$SO_3M$,
(iii) a group of the following formula (IV)

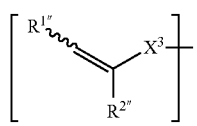
(IV)

wherein
$X^3$ is CO, —$CH_2CO$—, CS, or —$CH_2CS$—,
$R^{1''}$ and $R^{2''}$ which are independent from each other and independently have the same meaning as defined for $R^1$ and $R^2$ in formula (II), or
(iv) a group $[Z'X'']_mE$,
wherein
Z' is a straight chain or branched $C_{1-4}$ alkylene group,
X'' is an oxygen atom, a sulfur atom or NH,
E is a hydrogen atom,
$PO_3M_2$,
a straight chain or branched $C_{1-16}$ alkyl group which may be substituted by a $C_{3-6}$ cycloalkyl group, a $C_{6-14}$ aryl or $C_{3-14}$ heteroaryl group, —COOM, —$PO_3M$, —O—$PO_3M_2$ or —$SO_3M$,
a $C_{3-6}$ cycloalkyl group which may be substituted by a $C_{1-16}$ alkyl group, a $C_{6-14}$ aryl or $C_{3-14}$ heteroaryl group, —COOM, —$PO_3M$, —O—$PO_3M_2$ or —$SO_3M$,
a $C_{6-14}$ aryl or $C_{3-14}$ heteroaryl group which may be substituted by —COOM, —$PO_3M$, —O—$PO_3M_2$ or —$SO_3M$, and
m is an integer of from 1 to 10; and
wherein M of any one $R^1$, $R^2$, L, R and E, which M are independent from each other, each represent a hydrogen atom or a metal atom;

(b) 2 to 20 percent by weight based on the total weight of the composition of a polymerizable compound of the following formula (V):

$$A'\text{-}L'\text{-}A' \quad (V)$$

wherein the
A' which are independent from each other, each represent a group of the following formula (VI)

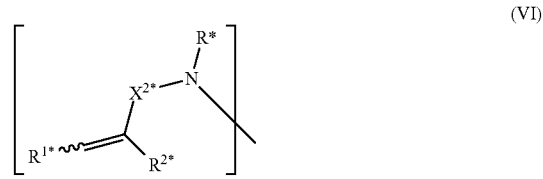
(VI)

wherein
$X^{2*}$ independently has the same meaning as defined for $X^1$ in formula (II),
$R^{1*}$ and $R^{2*}$ are independent from each other and independently have the same meaning as defined for $R^1$ and $R^2$ in formula (II),
R* is a hydrogen atom,
a straight chain or branched $C_{1-16}$ alkyl group which may be substituted by a $C_{3-6}$ cycloalkyl group, a $C_{6-14}$ aryl or $C_{3-14}$ heteroaryl group, —COOM, —$PO_3M$, —O—$PO_3M_2$ or —$SO_3M$,
a $C_{3-6}$ cycloalkyl group which may be substituted by a $C_{1-16}$ alkyl group, a $C_{6-14}$ aryl or $C_{3-14}$ heteroaryl group, —COOM, —$PO_3M$, —O—$PO_3M_2$ or —$SO_3M$,
a $C_{6-14}$ aryl or $C_{3-14}$ heteroaryl group which may be substituted by —COOM, —$PO_3M$, —O—$PO_3M_2$ or —$SO_3M$,
L' is a divalent $C_{2-12}$ alkylene linker group, which may contain 1 to 3 carbonyl groups or heteroatoms selected from oxygen, nitrogen and sulfur, and which may be substituted by a hydroxyl group, a $C_{6-14}$ aryl group, —COOM, —PO$_3$M, —O—PO$_3$M$_2$ or —SO$_3$M, wherein M is a hydrogen atom or a metal atom; wherein M of any one R$^{1*}$, R$^{2*}$, L' and R*, which M are independent from each other, each represent a hydrogen atom or a metal atom; and (c) 0.001 to 1 percent by weight based on the total weight of the composition of a stabilizer;

to form the aqueous dental composition having a pH of at most 7;

wherein the aqueous dental composition has storage stability for 30 days at 50° C.

* * * * *